(12) United States Patent  
Cheng et al.

(10) Patent No.: US 7,858,142 B2  
(45) Date of Patent: Dec. 28, 2010

(54) LAMININ-MODIFIED CONDUIT FOR NERVE REGENERATION AND METHODS OF MANUFACTURING THE CONDUIT AND REGENERATING NERVES USING THE CONDUIT

(75) Inventors: Henrich Cheng, No. 322, Sec. 2, Shih-Pai Road, Peitou, Taipei (TW) 11217; Yi-Cheng Huang, Taipei (TW); Pei-The Chang, Taipei (TW); Yi-You Huang, Taipei (TW)

(73) Assignee: Henrich Cheng, Taipei (TW)

( * ) Notice: Subject to any disclaimer, the term of this patent is extended or adjusted under 35 U.S.C. 154(b) by 1078 days.

(21) Appl. No.: 11/550,049

(22) Filed: Oct. 17, 2006

(65) Prior Publication Data

US 2008/0089922 A1    Apr. 17, 2008

(51) Int. Cl.  
*A61L 33/00* (2006.01)

(52) U.S. Cl. .............. 427/2.1; 623/17.16; 528/354; 427/2.14; 427/2.21; 427/2.24; 427/457; 427/532; 427/533; 427/535; 427/536; 427/569

(58) Field of Classification Search ............. 623/17.16; 528/354; 427/2.1  
See application file for complete search history.

(56) References Cited

U.S. PATENT DOCUMENTS

| 6,730,772 B2 * | 5/2004 | Shastri ............... 528/354 |
| 2007/0005140 A1 * | 1/2007 | Kim et al. ............ 623/17.16 |

FOREIGN PATENT DOCUMENTS

| CN | 1439432 A | | 9/2003 |
| CN | 1439432 A | * | 9/2003 |
| WO | 2007090102 A2 | | 8/2007 |

* cited by examiner

*Primary Examiner*—Michael Kornakov  
*Assistant Examiner*—Andrew Bowman  
(74) *Attorney, Agent, or Firm*—Panitch Schwarze Belisario & Nadel LLP

(57) ABSTRACT

A laminin-modified polymeric hollow conduit is provided for promoting nerve regeneration across the gap between severed ends of a nerve. The conduit is manufactured by a method involving gas plasma treatment. Utilizing the laminin-modified conduit, functional recovery has been achieved in mammals with a severed spinal cord.

16 Claims, 18 Drawing Sheets (a)

(b)

(c)

(a)

(b)

1 day    3 days (c)

1 day    3 days (a)

(b)

(a)

(b)

(a)

(b)

LAMININ-MODIFIED CONDUIT FOR NERVE REGENERATION AND METHODS OF MANUFACTURING THE CONDUIT AND REGENERATING NERVES USING THE CONDUIT

FIELD OF THE INVENTION

The present invention pertains to the field of mammalian nerve regeneration. More specifically, the present invention discloses a hollow conduit for promoting nerve regeneration across the gap between severed ends of a nerve. The present invention also discloses methods for making and using said conduit.

BACKGROUND OF THE INVENTION

Nerve regeneration is a complex biological phenomenon. Mature neurons do not replicate; in other words, they do not undergo cell division. Once the nervous system is impaired, it is very difficult to recover, and failures in other parts of the body may occur. In the peripheral nervous system (PNS), nerves can regenerate on their own if injuries are small. Even though regeneration occurs after injury to the adult PNS, it does not always result in functional recovery. This is primarily due to misdirection of regenerating axons toward an inappropriate target. When the nerve is separated by a gap greater than 1 cm in length, the lack of specific guidance can lead axons growing backwards into the proximal nerve stump, entering an inappropriate endoneurium, or forming neuromas. In all these conditions, injured axons can take several months to regenerate. To increase the prospects of axonal regeneration and functional recovery, numerous strategies have been used. These have included implantation of autografts, allografts, xenografts, and Schwann cell (SC)-filled tubes. A number of problems may arise from autologous grafting including: donor site morbidity, denervation distal to the donor site, neuroma formation and the fact that there are a limited number of suitable sites available for nerve harvesting. These disadvantages have led to the development of artificial nerve grafts.

Researches have focused on the creation of tubes, or nerve guides, to bridge the gap between transected nerves in both the CNS (central nervous system) and PNS. Of the numerous entubulation studies reported to date, some of the best results have been achieved in the PNS (S. E. Mackinnon and A. L. Dellon, *Plastic Reconstructive Surg*, 85: 419-24 (1990); M. F. Meek et al., *Microsurgery*, 19: 247-53 (1999); S. T. Li et al., *Clin Mater*, 9: 195-200 (1992)). In addition to the biodegradability and biocompatibility issues, the influence of a variety of physical parameters of the conduits, such as conduit diameter and length, lumenal surface microgeometry, and wall porosity and permeability have been established.

Introduction of cultured SCs into the lumen of a synthetic nerve graft enhances peripheral nerve regeneration (V. Guenard et al., *J Neurosci*, 12: 3310-20 (1992)). For SCs to survive in the graft, attachment is mandatory, since attachment is a prerequisite for survival and proliferation of SCs. Laminin, the extracellular matrix protein, is a permissive protein for SCs adhesion used in neural regeneration. Laminin can interact with the integrins on the SC surface and support SC attachment and proliferation. Madison et al. disclosed the use of a bioresorbable nerve guide filled with a laminin-containing gel to hasten axonal regeneration in mice (Madison et al., *Experimental Neurology*, 88: 767-772 (1985)). However, the manufacture of tubes filled with such promoting agents is a relatively expensive and tedious process. Rangappa et al. disclosed the use of a nerve guide filled with aligned laminin-coated poly(l-lactide) filaments to induce robust neurite growth and provide directional orientation (N. Rangappa et al., *J Biomed Mater Res*, 51: 625-34 (2000)). However, the arrangement of the filaments within the guidance channels is irregular and difficult to reproduce. U.S. Pat. Nos. 4,963,146 and 5,019,087 disclosed hollow conduits for promoting the in vivo regeneration of a severed mammalian nerve having walls comprised of Type I collagen and laminin-containing material, as well as methods for preparing such conduits. The methods comprise the steps of forming a dispersion containing Type I collagen and a laminin-containing material; adding a precipitating agent to the dispersion; and contacting the precipitate with a spinning mandrel to form a tubular collagen membrane.

Studies have suggested that the interactions between the biological environment and artificial materials are most likely dominated by the materials' "surface properties". Hence, surface modification of existing biomaterials with an aim towards improving a material's biocompatibility has been a major focus of biomaterials research in recent years. Several synthetic approaches, such as grafting long alkyl chains or bioactive molecules, have been attempted in different laboratories. These synthetic methods often lead to alterations of the original material's physical properties. In contrast, the plasma surface modification process has been shown to be able to modify the surface properties of a biomaterial without affecting its bulk physical properties. In addition, a wide range of chemicals, including those which are not polymerizable by conventional synthetic methods, can be used to incorporate specific functional groups into the substrate.

Gas plasma treatment is extensively used for chemical modification of poly(lactic acid) (PLA) or poly(lactic-co-glycolic acid) (PLGA). Nonpolymerizing gas plasma can create reactive sites such as peroxide and sulfonic acid groups on the surface of polymers. Plasma processes have been used to increase the hydrophilicity of PLA and to improve its cell adhesion (J. Yang et al., *Polym Adv Technol*, 13: 220-6 (2002)). As an alternative method, combining plasma treatment and collagen anchorage could also improve the cell affinity of PLA significantly (J. Yang et al., *Biomaterials*, 23: 2607-14 (2002)). Such results indicate that the surface composition and the functional groups on the surface of a polymer after plasma treatment had a great effect on the cell affinity of said polymer.

Although improved results in nerve regeneration have been obtained through the use of nerve guides/conduits comprising cell-adhesive molecules such as laminin, there is still much room for further improvement. Moreover, it would still be desirable to provide a means by which an even greater number of myelinated axons is regenerated, a faster rate of nerve growth is achieved, and longer nerve gaps are spanned. A need still exists to fulfill such a need and still reduce or eliminate problems that have been encountered with prior art nerve repair attempts such as revascularization, excessive fibrosis, reorientation of nerve fibers, and the final poor return of function of the end organs.

BRIEF SUMMARY OF THE INVENTION

By means of the present invention, a new conduit for nerve regeneration has been discovered which eliminates or substantially reduces many of the disadvantages and problems associated with the prior art attempts at nerve regeneration.

Accordingly, in a first aspect, the present invention provides a hollow conduit for promoting the in vivo regeneration of a severed mammalian nerve so as to bridge a gap between its severed ends, comprising a wall composed of a biodegradable polymeric material with laminin covalently bonded to the lumenal surface of the wall, wherein the bonding of the laminin is achieved through gas plasma treatment.

In another aspect, the present invention provides a method for making a laminin-modified conduit for promoting in vivo regeneration of a severed mammalian nerve so as to bridge a gap between its severed ends, comprising the steps of
  (a) treating a hollow conduit composed of a biodegradable polymeric material with gas plasma at appropriate power density and appropriate pressure for a sufficient time to activate the polymeric surface for bonding with laminin; and
  (b) contacting the lumenal surface of the conduit with laminin for a sufficient time to allow covalent bond formation between laminin and the polymeric surface.

In a further aspect, the present invention provides a method for promoting in vivo regeneration of a mammalian severed nerve so as to bridge a gap between its severed ends, comprising bringing the respective ends of the severed nerve into contact with each end of a hollow conduit comprising a wall composed of a biodegradable polymeric material with laminin covalently bonded to the lumenal surface of the wall, wherein the bonding of the laminin is achieved through gas plasma treatment.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 4 comprises FIGS. 4A and 4B showing the quantitative results of attachment of SCs on modified films.

FIG. 6 comprises FIGS. 6A and 6B.

FIG. 7 comprises FIGS. 7A and 7B showing the results of the behavior analyses.

FIG. 8 comprises FIGS. 8A to 8E showing the results of the immunohistochemical analyses.

DETAILED DESCRIPTION OF THE INVENTION

Figure 1A:
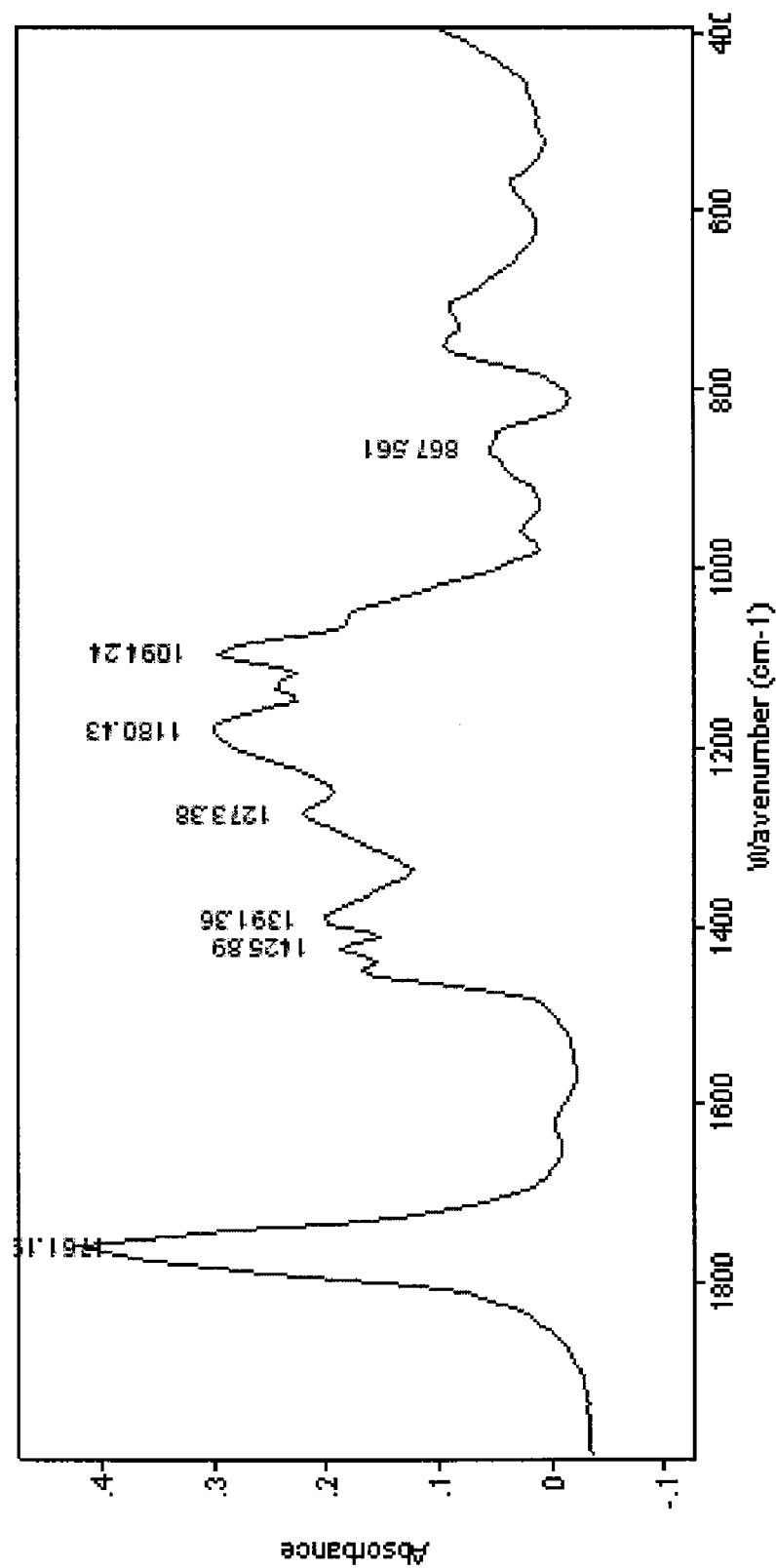
FIG. 1 shows the FTIR absorption spectra of laminin-modified films prepared by oxygen plasma treatment: (a) non-treated PLGA film; (b) laminin-PLGA film; (c) non-treated chitosan film; and (d) laminin-chitosan film.
Figure 1B:
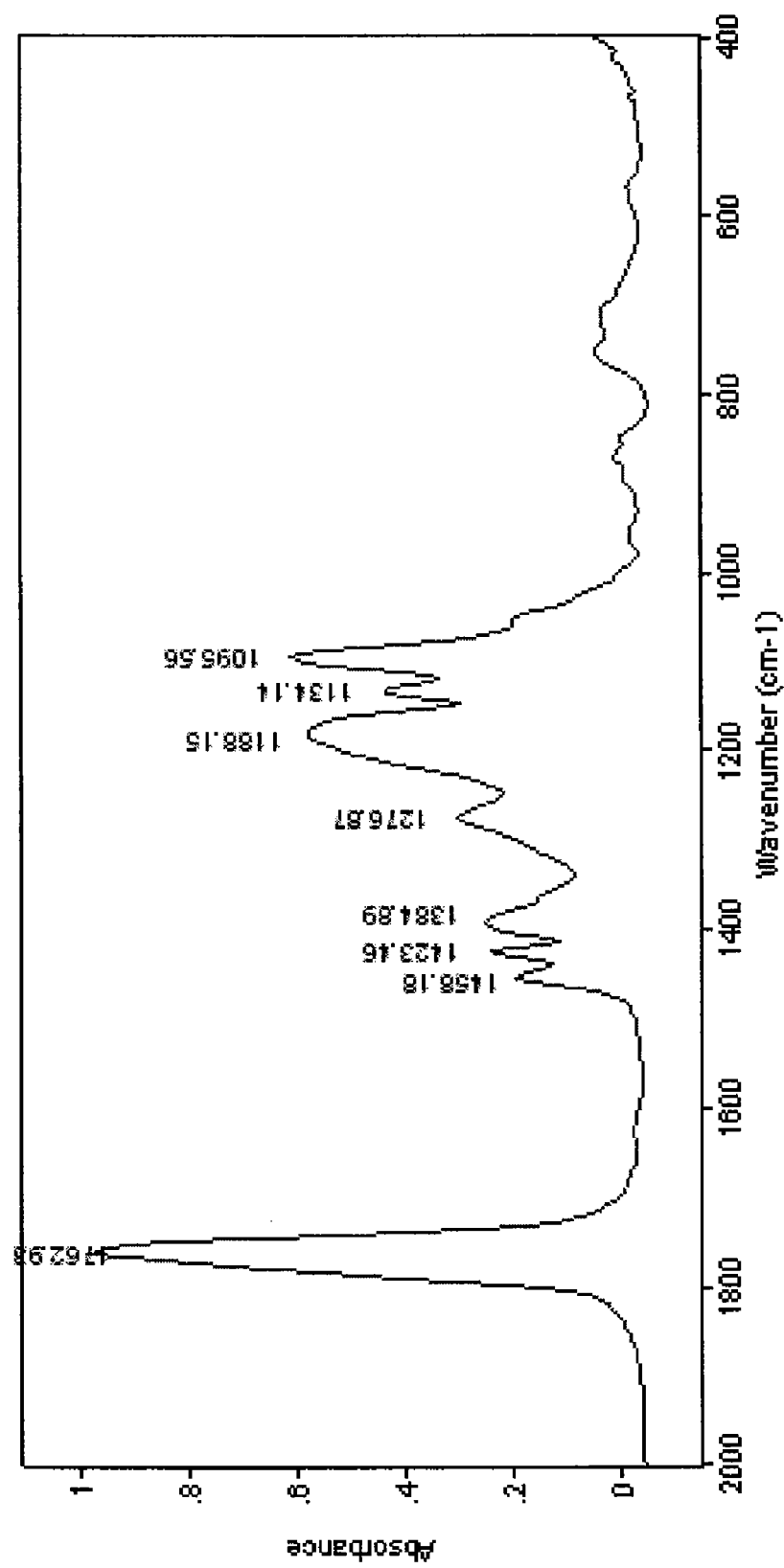
Figure 1C:
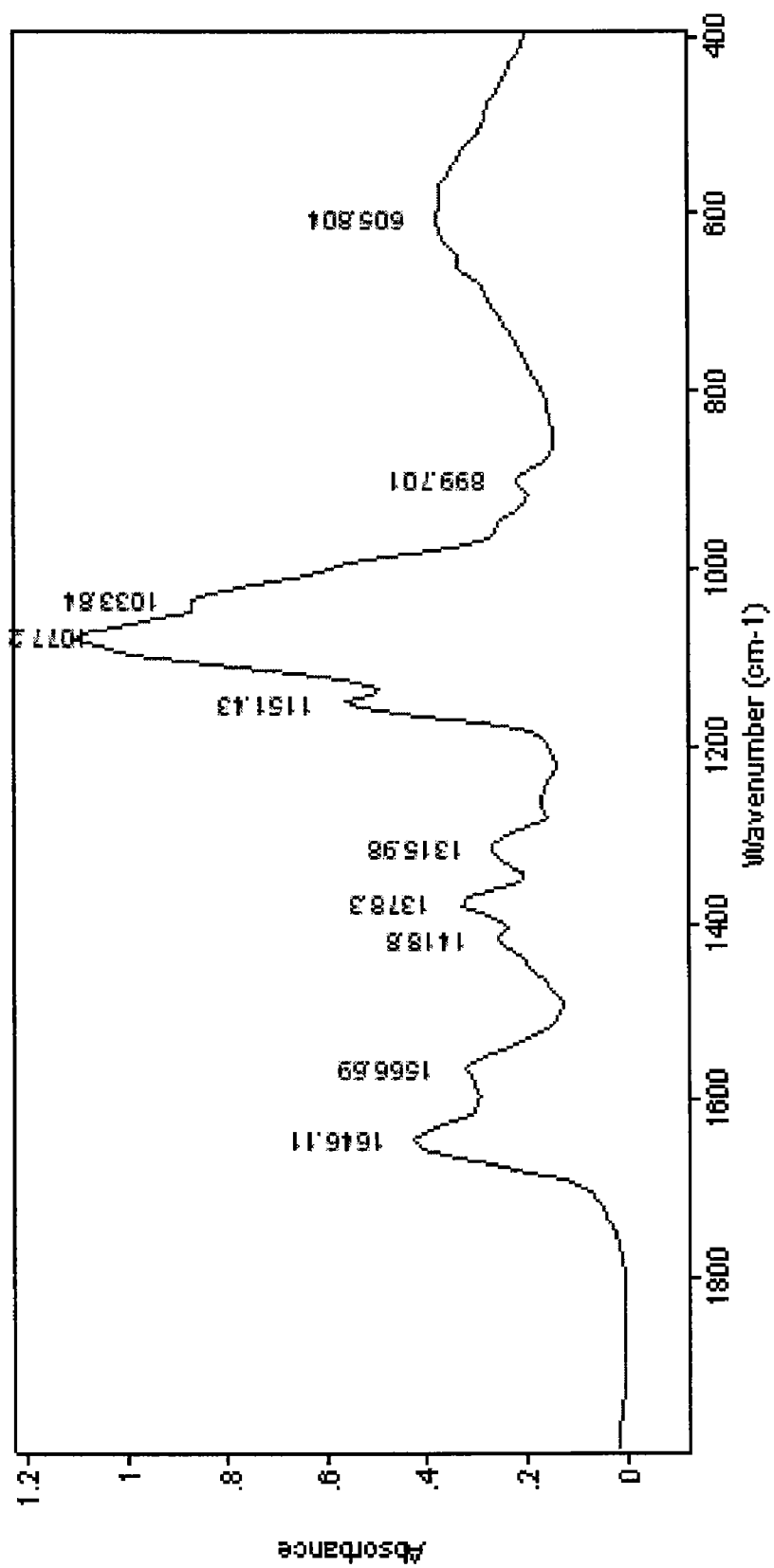
Figure 1D:
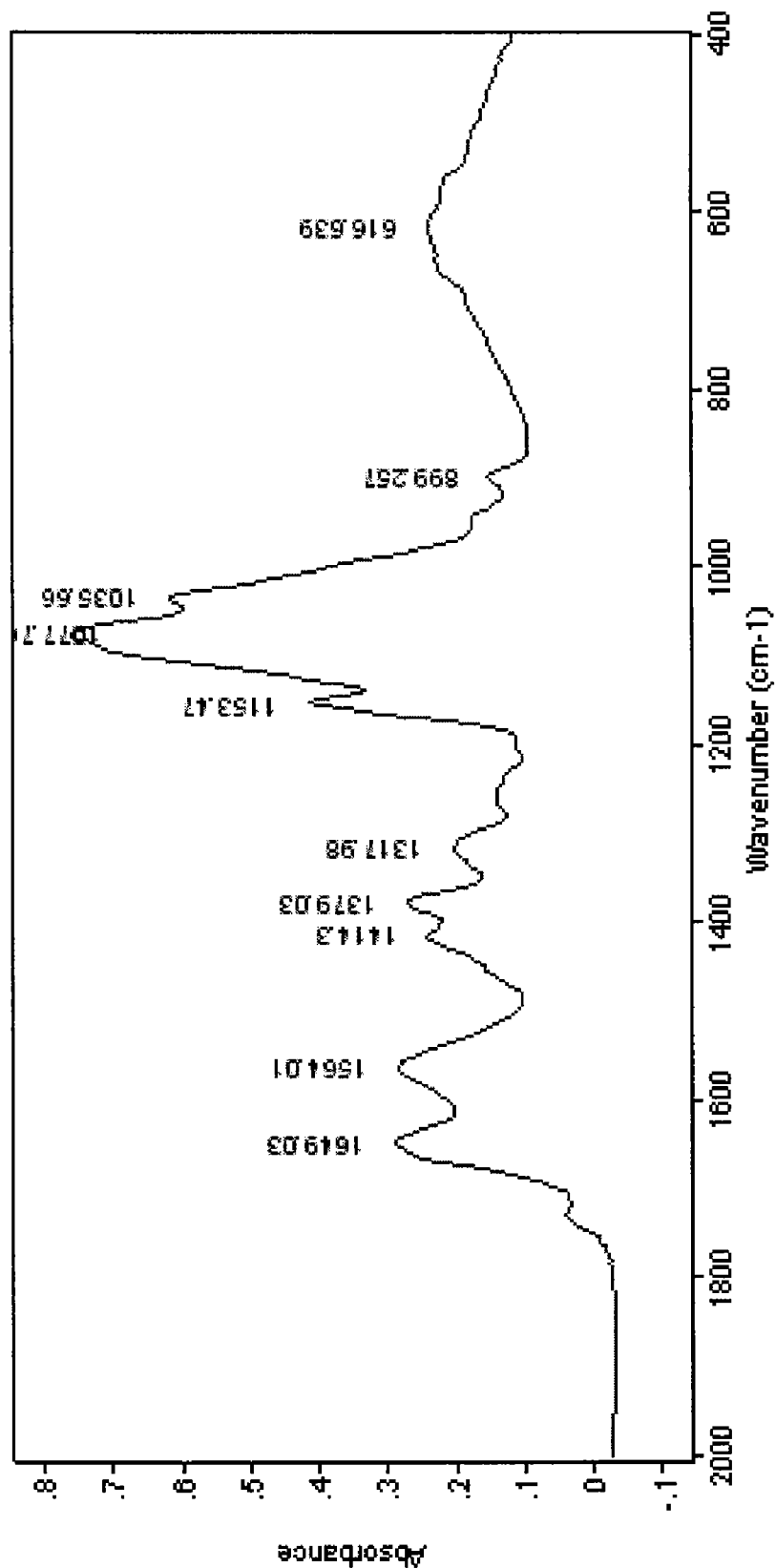

The present invention provides a hollow conduit for promoting the in vivo regeneration of a severed mammalian nerve so as to bridge a gap between its severed ends, comprising a wall composed of a biodegradable polymeric material with laminin covalently bonded to the lumenal surface of the wall, wherein the bonding of the laminin is achieved through gas plasma treatment.

According to the present invention, the biodegradable polymeric material refers to those conventionally used to make nerve conduits, including but not limited to collagen, poly(lactic acid) (PLA), poly(glycolic acid) (PGA), poly(lactic-co-glycolic acid) (PLGA), polycaprolactone, poly(caprolactone-co-lactic acid) (PCLA), chitosan, alginate, hyaluronic acid, gelatin, and fibrin. In a preferred embodiment of the present invention, the biodegradable polymeric material is PLGA or chitosan.

Laminin is an abundant component of all basement membranes. Basement membranes are thin, continuous sheets that separate epithelium from stroma and surround nerves, muscle fibers, smooth muscle cells and fat cells. Basement membranes contain, among other things, Type IV collagen, laminin, nidogen, heparin sulfate proteoglycan and other glycoproteins and proteoglycans. Human placenta, which contains a large quantity of laminin, is a good source of laminin.

Laminin may be extracted from materials such as basement membranes and human placenta by means well known to those skilled in the art. Such extraction techniques and a more detailed discussion on laminin is set forth by Rupert Timple, et al. in "Laminin," *Methods of Enzymology—Structural and Contractile Proteins, Part A. Extracellular Matrix*, Vol. 82. Chap. 47, pp. 831-838, Academic Press, (1982) and by Hynda K. Kleinman, et al. in "Biological Activities of Laminin," *Journal of Cellular Biochemistry*, Vol. 27, pp. 317-325 (1985); contents of both are incorporated herein by reference as if set out in fall.

Generally, the conduits of the present invention have an inner diameter in the range of about 100 µm to about 2000 µm. Preferably, the inner diameter of the conduit of the present invention is about 570 µm. The wall thickness of the conduits represents a balance between desired permeability and enough compressive strength to prevent collapse. Preferably, the conduits are made as thin as possible while still withstanding suturing and collapse when used in vivo. Suitably, the wall thickness of the conduits is in the range of about 0.5 mm to about 1.5 mm. Preferably, the wall thickness of the conduit of the present invention is between about 1 mm to about 1.2 mm. The length of the conduit varies with the length of the nerve gap that is to be bridged.

The present invention also provides a method for making a laminin-modified conduit for promoting in vivo regeneration of a severed mammalian nerve so as to bridge a gap between its severed ends, comprising the steps of:
  (a) treating a hollow conduit composed of a biodegradable polymeric material with gas plasma at appropriate power density and appropriate pressure for a sufficient time to activate the polymeric surface for bonding with laminin; and
  (b) contacting the lumenal surface of the conduit with laminin for a sufficient time to allow covalent bond formation between laminin and the polymeric surface.

According to the present invention, the hollow conduit used to make the laminin-modified conduit of the invention may be any commercially available conduit composed of a biodegradable polymeric material. Alternatively, the hollow conduit may be fabricated as needed by any known method, such as the fiber templating process of Flynn et al. as set forth in *Biomaterials* 24: 4265-4272 (2003), and the low-pressure injection molding process of Sundback et al. as set forth in *Biomaterials* 24: 819-830 (2003); contents of both are incorporated herein by reference as if set out in full.

In a preferred embodiment of the present invention, the hollow conduit is fabricated according to the lyophilizing and wire-heating process of Huang et al. as disclosed in *J. Biomed Mater Res Part B: Applied Materials* 74: 659-664 (2005), contents incorporated herein by reference as if set out in full. Briefly, a matrix (such as chitosan) solution is injected into a mold containing a metal (such as Ni—Cr) wire as the mandrel; the mold containing the matrix solution is put into a liquid nitrogen trap; after freezing, the mold is removed from liquid nitrogen and voltage is applied to the metal wire to heat it; once the matrix surrounding the wire melts slightly, the wire is pulled out from the matrix in order to create a longitudinally oriented channel in the matrix; the solvent may be removed by a lyophilizing method to form a conduit with a longitudinally oriented channel. Preferably, the hollow conduit used to make the laminin-modified conduit of the invention is made of chitosan or PLGA.

A plasma can be broadly defined as a gas containing charged and neutral species, including some of the following: electrons, positive ions, negative ions, radicals, atoms, and molecules. Plasma treatment is a popular method for modifying polymer surfaces. Such surface modification can be applied to achieve various purposes, such as producing special functional groups at the surface for specific interactions with other functional groups. An elaborate discussion of the plasma technique is provided by C.-M. Chan et al. in *Surface Science Reports* 24: 1-54 (1996), contents incorporated herein by reference as if set out in full.

According to the present invention, plasma treatment of a polymeric workpiece is achieved by placing the workpiece in contact with the gas to be used in the treatment and imposing high-energy radiation at a radio frequency, preferably about 13.56 MHz, sufficient to ionize the gas to a plasma state. While not intending to be bound by any particular theory or mechanism of operation, it is believed that the plasma activates the polymer chains that are in contact with the plasma by dissociating covalent bonds in the polymer chains to form free radicals that are reactive with each other or with free radicals in the plasma gas itself.

Different types of gases such as argon, oxygen, nitrogen, fluorine, carbon dioxide, and water can produce unique surface properties required by various applications. According to the present invention, the gas plasma used to treat the hollow conduit is preferably $O_2$ or $O_2$-containing gas plasma. It is well known that oxygen plasma can react with a wide range of polymers to produce a variety of oxygen functional groups, such as C—O, C=O, O—C=O and $CO_3$ at the surface. It is believed that the oxygen functional groups produced by the oxygen plasma on the polymer surface react with the —$NH_2$ groups of laminin, resulting in the binding of laminin to the lumenal surface of the conduit.

The effect of the plasma treatment of the present invention depends not only on the type of gas used to generate the plasma, but also on operating conditions, such as the power density, exposure time, working pressure, gas flow rate, temperature, electrode spacing, chamber dimensions, substrate bias voltage, or combinations of these conditions. According to the present invention, best results will be obtained using a power density, expressed in terms of wattage per unit area of the surface to be treated, ranging from about 2 to about 100 $W/cm^2$. In a preferred embodiment of the present invention, the power density used is about 50 $W/cm^2$. The plasma used in the present invention is preferably low-pressure plasma, that is, the gas pressure ranges from several mTorr to several hundred Torr. According to the present invention, best results will be obtained using a pressure ranging from about 0 mTorr to about 80 mTorr. In a preferred embodiment of the present invention, the pressure used is about 36 mTorr. Exposure time may be selected between about 5 to about 10 minutes, as long as the plasma treatment is sufficient to activate the polymer surface while not destroying the micro-structure of the polymeric material. In a preferred embodiment of the present invention, the exposure time is about 5 minutes. Other treatment conditions, such as the temperature and gas flow rate, are variable and not critical to the novelty or utility of the present invention.

According to the present invention, contacting the lumenal surface of the plasma-treated conduit with laminin may be achieved through any suitable method. For example, a solution containing an appropriate concentration of laminin may be added to the conduit. The amount of the laminin solution should be enough to immerse the conduit. Reaction conditions, such as time and temperature, for covalent bond formation between laminin and the polymeric surface depend on the species of the polymer, and can be determined by persons of ordinary skills in the art without undue experimentation in view of the present disclosure. In an embodiment of the present invention, the conduit is incubated in 200 μl of a 100 μg/ml laminin solution at 4° C. for 3 hours.

The present invention further provides a method for promoting in vivo regeneration of a mammalian severed nerve so as to bridge a gap between its severed ends, comprising bringing the severed ends of the nerve into contact with respective ends of a hollow conduit comprising a wall composed of a biodegradable polymeric material with laminin covalently bonded to the lumenal surface of the wall, wherein the bonding of the laminin is achieved by gas plasma treatment.

The laminin-modified conduit of the present invention is suitable for bridging severed nerves and promoting nerve regeneration and functional recovery in both PNS and CNS. In use, the severed ends of a nerve are brought into contact with respective ends of the conduit of the present invention, which is slightly longer than the gap to be bridged, so that no tension is placed upon the severed nerve. Both the distal and proximal nerve stumps are partially inserted into the conduit. Due to the flexibility of the conduit, it can be kept in the gap without suturing. However, the severed ends may also be sutured to the conduit over their perineurium, if necessary.

Example 1

Preparation and Characterization of Laminin-Modified Polymer Films 1.1 Preparation of Polymer Films Two kinds of polymer films were prepared. For the PLGA (Poly(d,l-lactide-co-glycolide) film, PLGA purchased from Sigma Chemcial Co., USA (50:50; Mw: 40,000~75,000) was dissolved in Dioxane with gentle stirring to make a 5% (wt/vol) solution. Then, 250 μl of this solution was added into a 96 well microplate, making it soaked around the bottom. The solvent was evaporated in air at room temperature and dry PLGA films were obtained.

For the chitosan film, chitosan/acetic acid solution (2% w/v) was used instead. Chitosan (Mw: 645,000) with a degree of deacetylation>85% was supplied by Sigma Chemical Co. Acetic acid (98%) was purchased from Wako Pure Chemical Industries Ltd. The process that followed is the same as the PLGA film. Water was distilled and deionized using a Millipore Milli-RO 10 Plus filtration system at 18 MΩ resistance.

1.2 Laminin-Modification of Polymer Films

To make the PLGA film hydrophilic and chemically active, the PLGA film was first treated with argon plasma. The plasma treatment was performed between two parallel plate electrodes in a glow discharge quartz reactor (Model SP100 Plasma System) manufactured by Anatech Co. Ltd., USA. The plasma power supply was set at 50 W at a frequency of 13.56 MHz. The substrates were placed on the ground electrode facing upward and exposed to the glow discharge at an argon pressure of 36 mTorr for 10 mins for the subsequent laminin (L-2020; Sigma, St. Louis, Mo.) coupling reaction. Then, 200 μl of laminin solution (100 μg/ml) was added onto the plasma pretreated PLGA film in a 96 well microplate at 4° C. for 3 hrs. After the coupling reaction, the laminin-PLGA films were washed with PBS buffer several times. BCA protein assay kit (Pierce, Rockford, Ill.) was used to calculate the amount of laminin immobilized on the PLGA surface.

The chitosan film was first washed by 1:1 0.1 M NaOH-MeOH and 1:1 MeOH-water to neutralize the acid, and then dried in the air. The subsequent process was the same as that for the PLGA film. Besides argon plasma, oxygen plasma was also used in these experiments.

As a comparison, laminin modification was also performed by the following chemical method. First, 200 μl of 100 mM 1-ethyl-3-(3-dimethylaminopropyl)-carbodiimide, hydrochloride (WSC, 39391, Sigma) was added to the PLGA film for 1 hr to activate its carboxyl groups. After being washed with PBS, the film was reacted with 200 ul laminin solution (100 ug/ml) for 3 hrs at 4° C. and subsequently washed by PBS buffer several times. BCA protein assay kit was used to calculate the amount of laminin after reacting and PBS washing.

To prepare a chemically-modified laminin-chitosan film, carboxyl groups must be introduced to chitosan first. 20 wt % NaOH (~50 μl) and 10 wt % monochloroacetic acid solution (~200 μl) were added in order at room temperature until the pH was 7.4±0.2. After that, the film was washed with PBS several times. The subsequent process was the same as that for the laminin-PLGA film.

The laminin-modified polymer films were divided into five groups: (1) films soaked in 100 μg/ml laminin for 3 hrs at 4° C., and then washed three times with PBS (laminin physically adsorbed on films, $L_{phys}$); (2) films soaked in 100 μg/ml laminin for 3 hrs at 4° C. after adding WSC to activate the carboxyl group, and then washed three times with PBS (laminin immobilized on films, through both physical absorption and chemical bonding, $L_{tot}$); (3) films soaked in 100 μg/ml laminin after $O_2$ or Ar plasma treatment ($L_{O2}$ and $L_{Ar}$); (4) blank films; and (5) petri dish as the control group. The percentage of laminin immobilized on films was calculated using:

$$P\% = (A_{Laminin}/A_0) \times 100\%,$$

where $A_{Laminin}$ is the absorption of laminin immobilized films and $A_0$ is the absorption of 100 μg/ml laminin.

To confirm if laminin has been successfully grafted onto the PLGA and chitosan surfaces, BCA protein assay was employed to calculate the amount of laminin. According to Table 1, the percentage of laminin immobilized on PLGA is higher than that on chitosan. Furthermore, the results also show that most of laminin immobilized on films by means of physical adsorption. As for plasma treatment, the efficiency of $O_2$ plasma is significantly higher than Ar plasma on both materials. The percentage of laminin immobilized on PLGA film by chemical method is almost the same as using $O_2$ plasma treatment. The amount of laminin on PLGA film is 41.3 μg/cm², but for the laminin-chitosan film, the efficiency of $O_2$ plasma treatment is higher. The amount of laminin on the chitosan film is 30.6 μg/cm². Chitosan films swell in water solution because of their low mechanical strength which made laminin modification by the chemical method difficult to control. In conclusion of the above, when compared with the traditionally used chemical method, $O_2$ plasma is a better method for surface modification.

TABLE 1

Percentages of laminin immobilized on both films determined by BCA assay.

|  | $L_{phys}$ | $L_{tot}$ | $L_{O2}$ | $L_{Ar}$ |
| --- | --- | --- | --- | --- |
| PLGA | 45.5% | 66.1% | 64.4% | 51.1% |
| Chitosan | 33.3% | 37.8% | 48.9% | 37.8% |

1.3 Characterization of Modified Surfaces

Fourier transfer infrared spectrometer (FTIR) was used to further characterize the surface modification of all films. All spectra were collected at a resolution of 4/cm and 16 scans and analyzed with built-in standard software package (Perkin-Elmer Spectrum One, Perkin-Elmer Co., Norwalk, Conn., USA).

FIG. 1 shows the FTIR absorption spectra for the films. For the laminin-PLGA film, the peak of absorption spectra at 1458 $cm^{-1}$ increased apparently because of the amide group (—CO—NH—R). The other peak at 1134 $cm^{-1}$ is due to amide (CO—$NH_2$) and amine (—$CH_2NH_2$) groups. Because of the alkane group, there is absorption of these peaks on PLGA film. For the chitosan and laminin-chitosan films, the ratio of peaks at 1564 $cm^{-1}$ to 1649 $cm^{-1}$ shows a significant increase. The absorption peak at 1649 $cm^{-1}$ indicates the existence of both amide and amine groups, but only amide groups can absorb at 1564 $cm^{-1}$. The percentage change of the two peaks indicates the formation of amide groups and disruption of amine groups. In other words, laminin has successfully immobilized on both PLGA and chitosan films.

In addition, the surface chemical composition of the PLGA and chitosan films was investigated by high resolution X-ray photoelectron spectroscopy (XPS, VG MICROTECH, MT-500, U.K.). The spectra were acquired on a VG Escalab 220i-x1 spectrometer with a monochromatic Mg-Ka radiation source (1253.6 eV) at a power of 400 W. CLAM4 MCD Electron Analyzer with a nine-channel detector was used. High-resolution detailed scans of the C1s peak region (275-295 eV) and N1s peak region (390-415 eV) were recorded with a pass energy of 20 eV. Concentrations of the various C1s and N1s peaks were calculated from the relative peak areas.

Figure 2A:
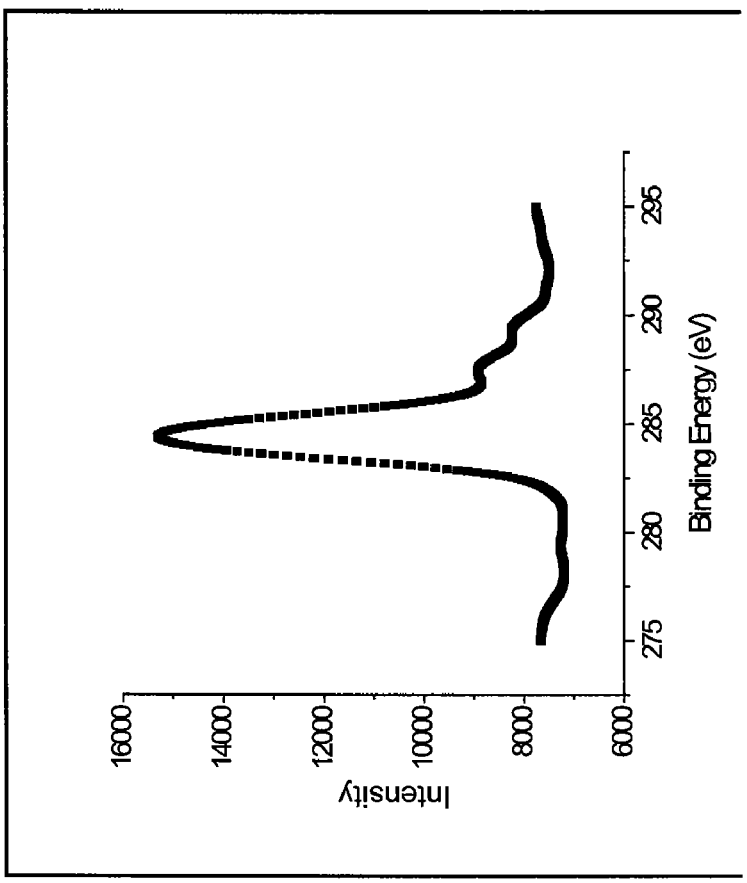
FIG. 2 shows the XPS spectra of laminin-modified films prepared by either the chemical method or oxygen plasma treatment: (a) XPS C1s core level spectra of the laminin-PLGA film prepared by the chemical method, wherein the left panel is the non-treated PLGA film and the right panel is the laminin-PLGA film; (b) XPS N1s core level spectra of the laminin-PLGA film prepared by the chemical method, wherein the left panel is the non-treated PLGA film and the right panel is the laminin-PLGA film; and (c) XPS C1s core level spectra of the laminin-chitosan film prepared by oxygen plasma treatment, wherein the left panel is the non-treated chitosan film and the right panel is the laminin-chitosan film.
Figure 2A:
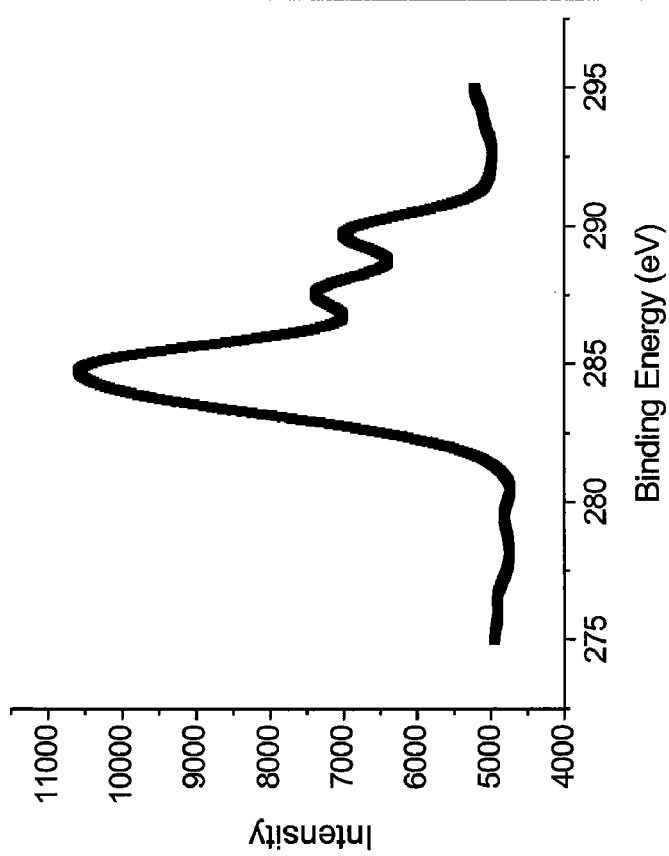
Figure 2B:
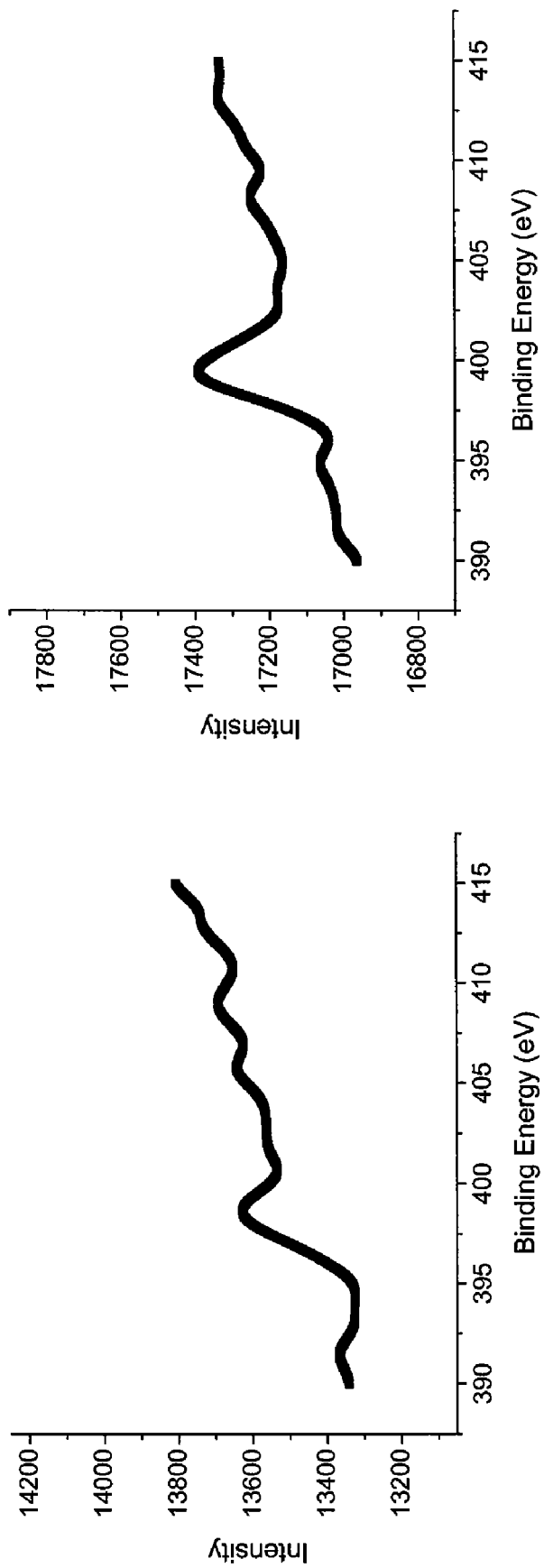
Figure 2C:
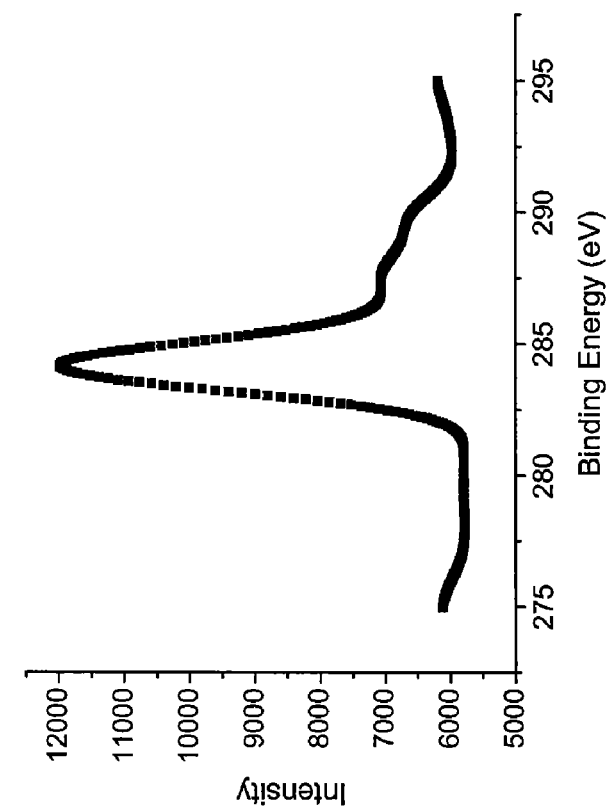
Figure 2C:
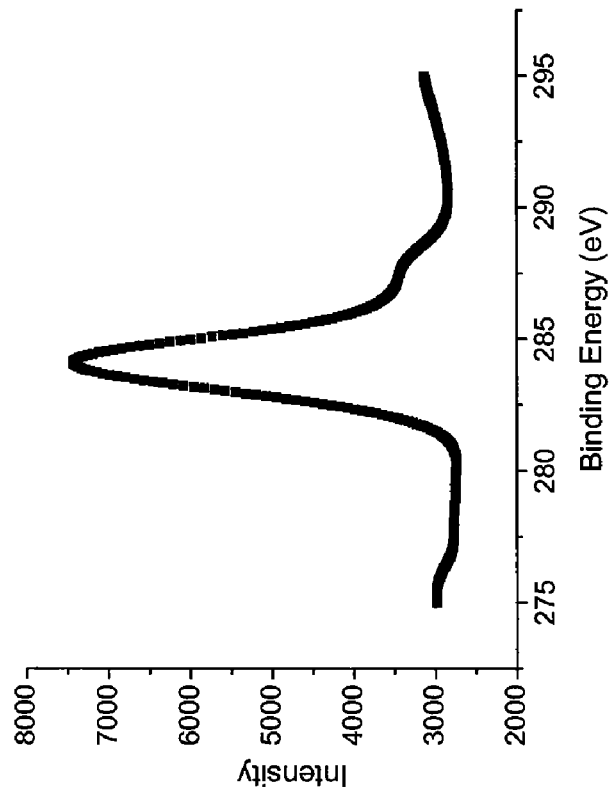

High-resolution XPS measurements were employed to study the surface chemical changes of films before and after laminin modification. The C1s region of PLGA films with and without laminin show three peaks (FIG. 2(a)). The first peak (284.5 eV) was attributed to the C1s of the aliphatic carbon bonds or carbon-hydrogen bonds (—CH, —C—C—). The second peak (287.5 eV) was attributed to the C1s of ether bonds (—C—O—) and —C—N bonds, and the third peak (289.6 eV) was ascribed to the C1s of carbonyl-like species, i.e. —COO—, >C=O or —COOH. However, the relative composition of the three types of C1s changed after laminin adhesion, as shown in Table 2. Two different features could be observed. First, the fraction of —CO and —CN bonds increased to 13.7%. Second, the fraction of aliphatic carbon bonds or carbon-hydrogen bonds increased to 80.3%. Third, the fraction of ester bonds decreased. The decrease in —COO—, —COOH bonds and increase in —CN bonds may have been caused by the cleavage of the ester bonds and formation of amide or amine bonds. The increase in —N—H and —N—C— bonds of N1s XPS spectra also supports this speculation (Table 2 and FIG. 2(b)). This shows that covalent bonds were formed between laminin and PLGA film. The C1s XPS spectra of Chitosan films with and without laminin were shown in FIG. 2(c). The —C—N— and carbonyl bonds increased significantly with decreasing —C—H and —C—C— bonds (Table 2). These results may stem from the breaking of aliphatic carbon or carbon-hydrogen bonds and creation of amide bonds. Laminin was covalently bonded onto the chitosan film shown by the XPS spectra that is the same as that from the FTIR absorption spectra. Since —N—H and —N—C— bonds existed in both chitosan and laminin-chitosan films, the N1s XPS spectra were not shown.

TABLE 2

Fraction of carbon functional groups from high-resolution C1s XPS and N1s XPS peaks of samples before and after laminin immobilization.

| Sample | (C1s)284.5 eV —C—H, —C—C-(%) | (C1s)287.5 eV —C—O—, —C—N(%) | (C1s)289.6 eV —COO—, >C=O, —COOH (%) | (N1s)399.4 eV —N—H, —N—C-(%) |
|---|---|---|---|---|
| PLGA | 72.4 | 12.6 | 14.1 | 0.5 |
| Laminin-PLGA | 80.3 | 13.7 | 3.5 | 1.1 |
| Chitosan | 84.3 | 12.8 | — | — |
| Laminin-Chitosan | 68.5 | 26.8 | 2.34 | — |

1.4 Adhesion and Proliferation of Schwann Cells on Modified Surfaces

The cell affinity of the laminin-modified films was verified by Schwann cell (SC) culturing. Schwann cells from adult female Wistar rats were isolated and expended in culture using methods proposed by J. P. Brockes et al., *Brain Research*. 165: 105-118 (1979). Briefly, the adult female Wistar rat was sacrificed by overdose anesthesia. The left and right sciatic nerve were resected, washed by phosphate-buffer saline (PBS), and cut into pieces of 1 mm in length. The fragments were treated by enzymatic digestion with 0.03% collagenase/0.25% trypsin in 3 ml of Dulbecco modified Eagle medium (DMEM) and incubated in 5% $CO_2$ at 37° C. for 30 mins. After incubation, the fragments were centrifuged at 2000 rpm and the supernatant was removed. The epineuriums were mechanically dissociated by needle. Primary cell suspension was plated in DMEM with 10% heat-inactivated fetal bovine serum (FBS) and 1% antibiotics (penicillin-streptomycin solution and amphotericin B) in a petri dish. The culture medium was replaced twice per week and the individual nerve fragments were transplanted to new dishes once per week for higher cell concentration during cell suspension. Then, $2\times10^4$ cells/ml Schwann cells were seeded in individual wells of a 96-well tissue culture plate with medium of 2 ml DMEM with 10% FBS after suspension to test the effects of various PLGA and chitosan films on the growth of Schwann cells.

Scanning electron microscopy (SEM) and optical microscopy (Olympus IX70) were used for Schwann cells morphology evaluation. For SEM observation, all specimens had to be fixed and dehydrated through the processes below. First, the PLGA and chitosan films were immersed in 2% glutaraldehyde in PBS for 1 h to fix. Then, a series of ascending alcohol solutions, commencing at 50%, were used to dehydrate the films. Critical point drier (CPD) was than applied for specimen drying. All specimens were than examined by SEM after being gold coated. The results obtained by SEM were not shown herein.

Figure 3:
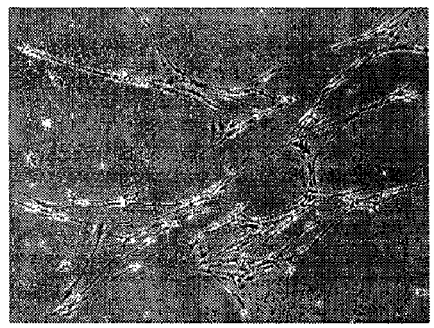
FIG. 3 shows the microscopic photos of Schwann cells (SCs): (a) morphological appearances SCs cultured on petri dishes; and attachment of SCs on the modified films—morphological appearances of SCs on laminin-chitosan films with (b) and without (c) oxygen plasma treatment, 1 and 3 days after seeding.
Figure 3:
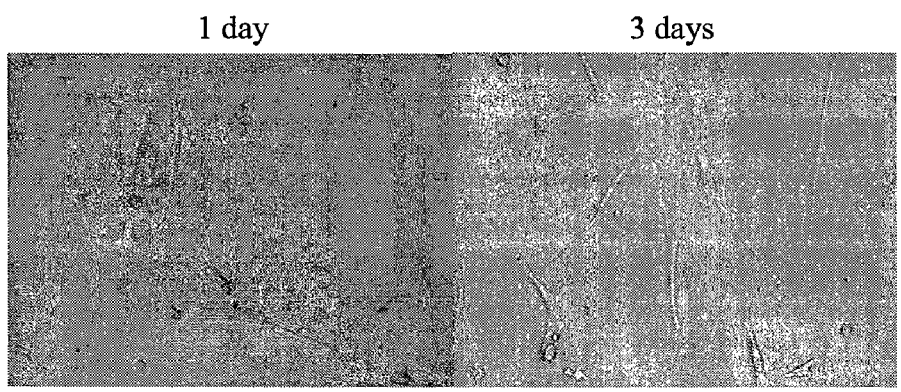
Figure 3:
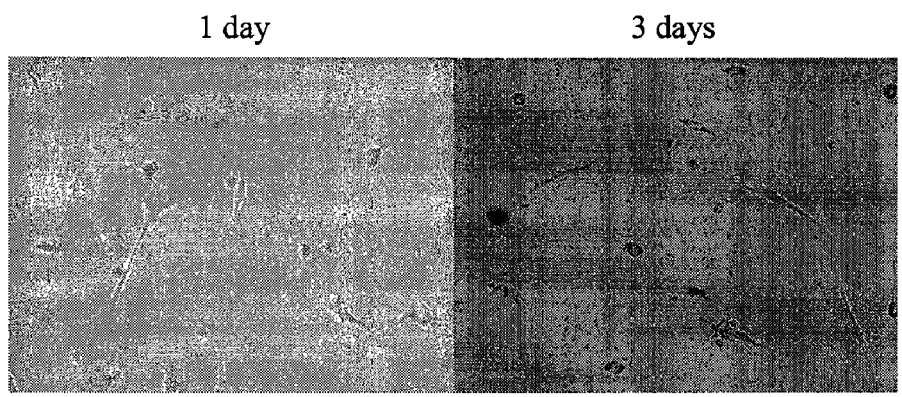

Purification by the sequential explanation method resulted in highly purified SC cultures (FIG. 3(a)). Most cells stretched out and then transformed to a spindle shape, although there were also a considerable number of cells that appeared partially folded, indicating that the cells were not yet fully attached.

At 1 day after seeding, most SCs adhering to the modified films demonstrated small lamellipodial extensions (FIGS. 3(b) and (c), left panel). At 3 days, most cells stretched out or transformed to a spindle shape on the $O_2$ plasma treated laminin-chitosan film (FIGS. 3(b) and (c), right panel). On the laminin-chitosan film without plasma treatment, a lot of cells were still not fully stretched even after a long time. Historically, SCs were described to be spindle-shaped. However, in later years it was demonstrated that, although many of cultured SCs have this characteristic spindle-shaped morphology, some have a more flattened (fibroblast-like) morphology.

Cell activity was quantified using the MTS assay (CellTiter 96™ Aqueous, Promega). At each time point, 40 μl of MTS reagent and 600 μl of culture medium were added to each well. Plates were incubated at 37° C., 5% $CO_2$ for 4 h. The absorbance at a wavelength of 490 nm was measured by UV/VIS spectrometer (Lambda 20, Perkin Elmer), and the mean of the readings was also taken. Background absorbance was corrected by subtracting the absorbance index of culture medium from the data.

Figure 4A:
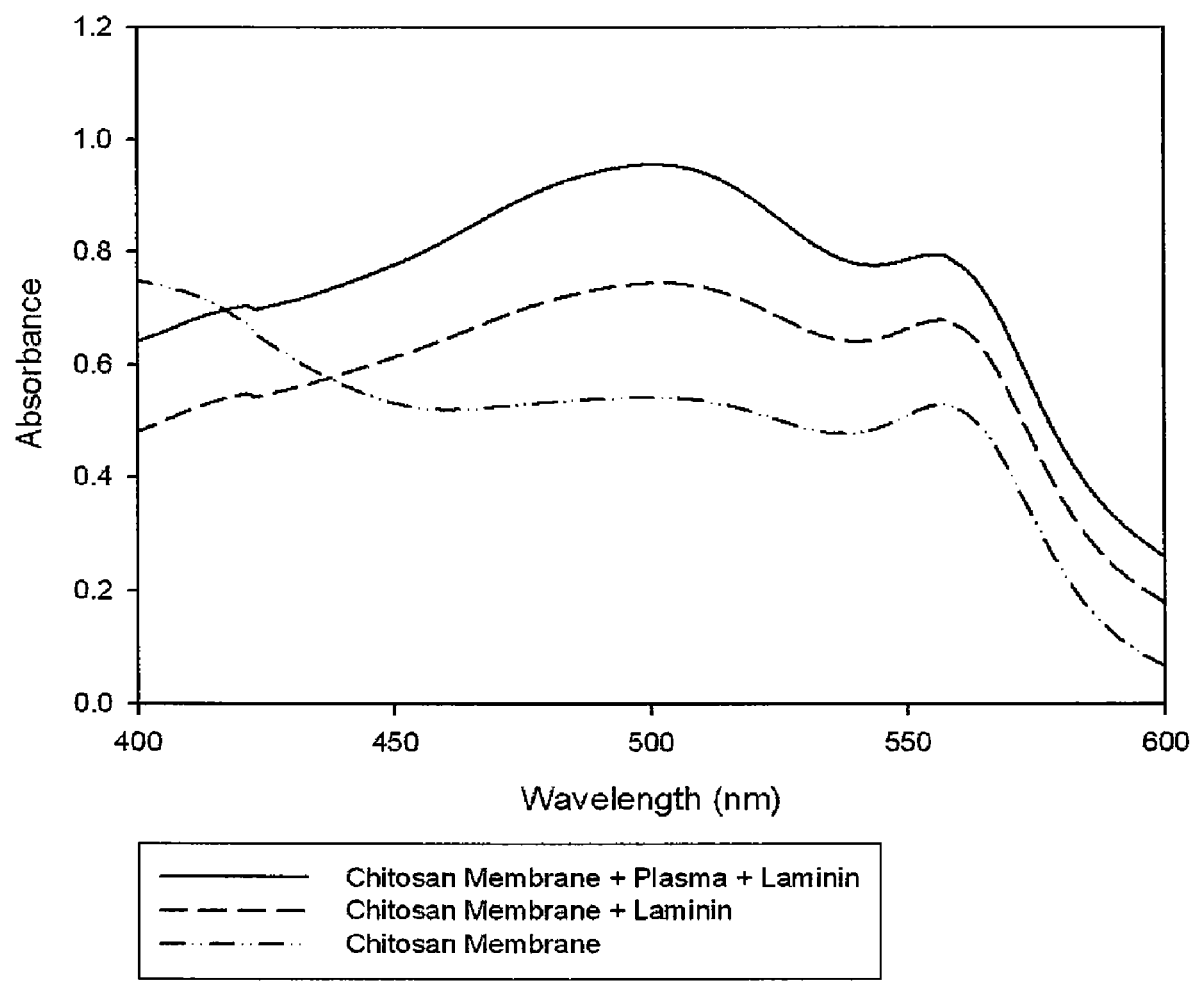
FIG. 4A is the result of the MTS test of SCs adhering to different films at 10 days after seeding. The number of cells seeded was about $1 \times 10^5$ cells/well. The three modified films were compared among each other.
Figure 4B:
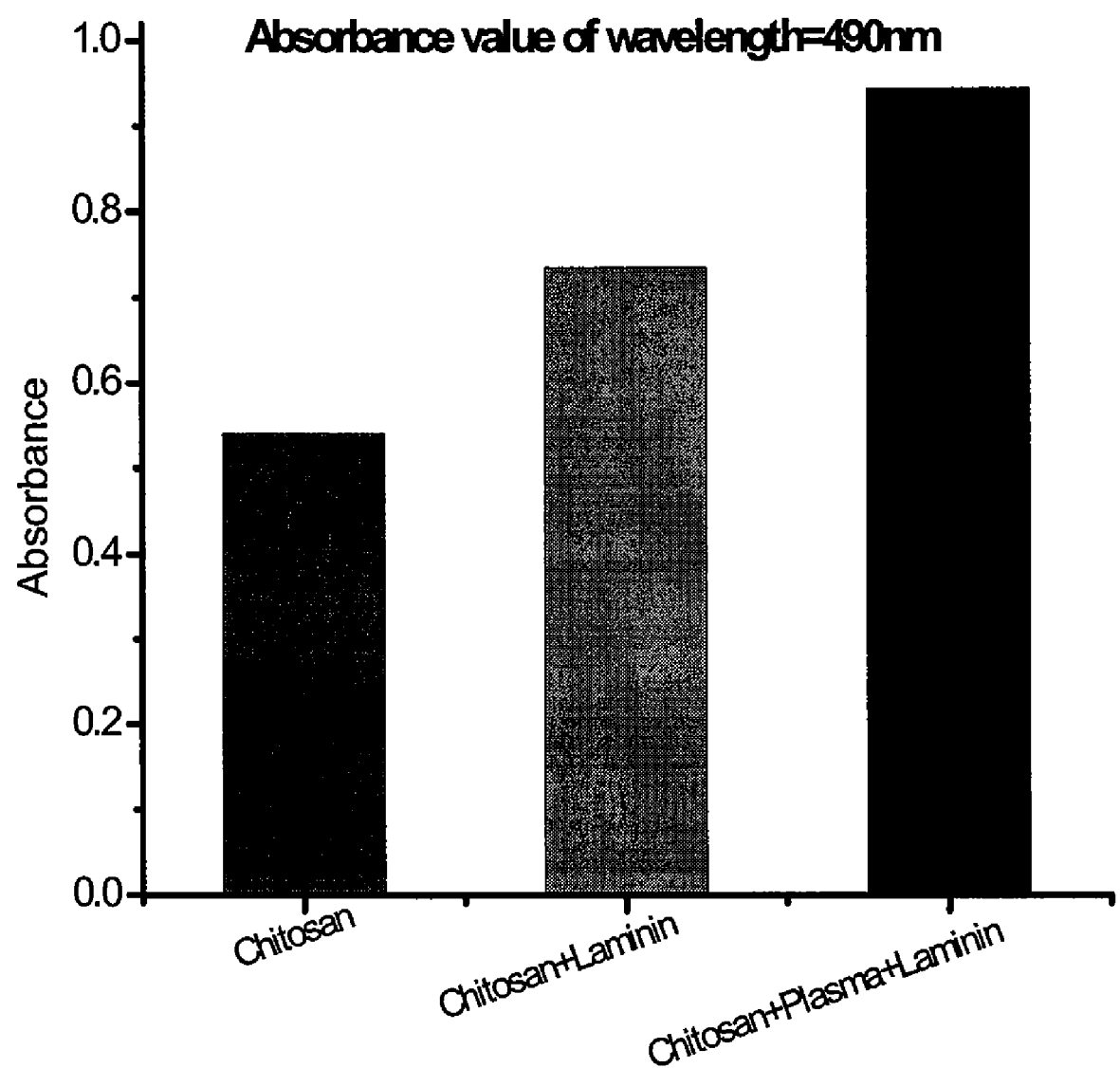
FIG. 4B shows the relative ratio of cell viability on the three films. The absorbance wavelength is 490 nm. "Chitosan+plasma+Laminin": oxygen plasma treated laminin-chitosan film. "Chitiosan+plasma": laminin-chitosan film without oxygen plasma treatment. "Chitosan": Chitosan film only.

The quantity of adhering cells differed among the modified films (FIG. 4). At 10 days after seeding, the number of cells adhering to the $O_2$ plasma treated laminin-chitosan film is significantly higher compared to the other films. Moreover, the same results were obtained from the diagram by calculating cell viabilities on the modified films.

1.5 Conclusions

This study showed that using oxygen plasma for surface modification is easier to control, more straightforward, and more effective. Compared with the conventional chemical method, the percentage of laminin incorporated on chitosan films by plasma treatment is significantly higher. Most of laminin adsorbed on films by physical adsorption. Using FTIR and XPS, laminin was shown to be immobilized onto the surface of both films. The results of XPS spectra indicate covalent bonding between laminin and the surface were formed. Laminin on the surface of chitosan and/or PLGA films had a great effect on the attachment and affinity of Schwann cells. These successful results are deemed important for directing peripheral nerve regeneration.

Example 2

Functional Recovery Following Traumatic Spinal Cord Injury Mediated by Laminin-Modified Nerve Conduit 2.1 Materials Chitosan, with average molecular weight of about 645,000, was supplied by Sigma Chemical Co. The degree of deacetylation (DDA) was determined to be 82.5±1.15% by $^1$H-NMR spectroscopy. Deuterium oxide ($D_2O$, L-4501) and deuterium chloride (DCl, 35 wt % in $D_2O$) was purchased from Sigma-Aldrich (USA). Acetic acid (98%, Wako Pure Chemical Industries LTD) and Ni—Cr wire (570 um) were used as received. All other chemicals and solvents were purchased from Sigma-Aldrich (Oakville, Canada) and used as received unless otherwise noted. Water was distilled and deionized using a Millipore Milli-RO 10 Plus filtration system at 18 MΩ resistance.

2.2 Analysis of the Degree of Deacetylation (DDA)

Chitosan with a DDA of 96.4±0.72% was synthesized by immersing commercially available 82.5±1.15% deacetylated chitosan flakes in a 40% aqueous solution of sodium hydroxide for 2 h at 110° C. The DDA of chitosan samples was determined using $^1$H-NMR spectroscopy (Bruker AV400 MHz) according to a modified published procedure (see L. Vachoud et al., *Carbohydr Res* 1997; 302: 169-177; and M. Lavertu et al., *J Pharm Biomed Anal* 2003; 32: 1149-1158). Briefly, samples were prepared by stirring at room temperature 10 mg of chitosan in a solution composed of 1.96 ml of $D_2O$ and 0.04 ml of DCl and waiting about half an hour to ensure complete dissolution of the polymer. The concentration of polymer in the solution was approximately 0.5% (w/v) in all cases. The DDA was calculated by comparing the integrated area of the signal group of H1 or H2-H6 with that of the signal of the methyl group as previously described.

Figure 5A:
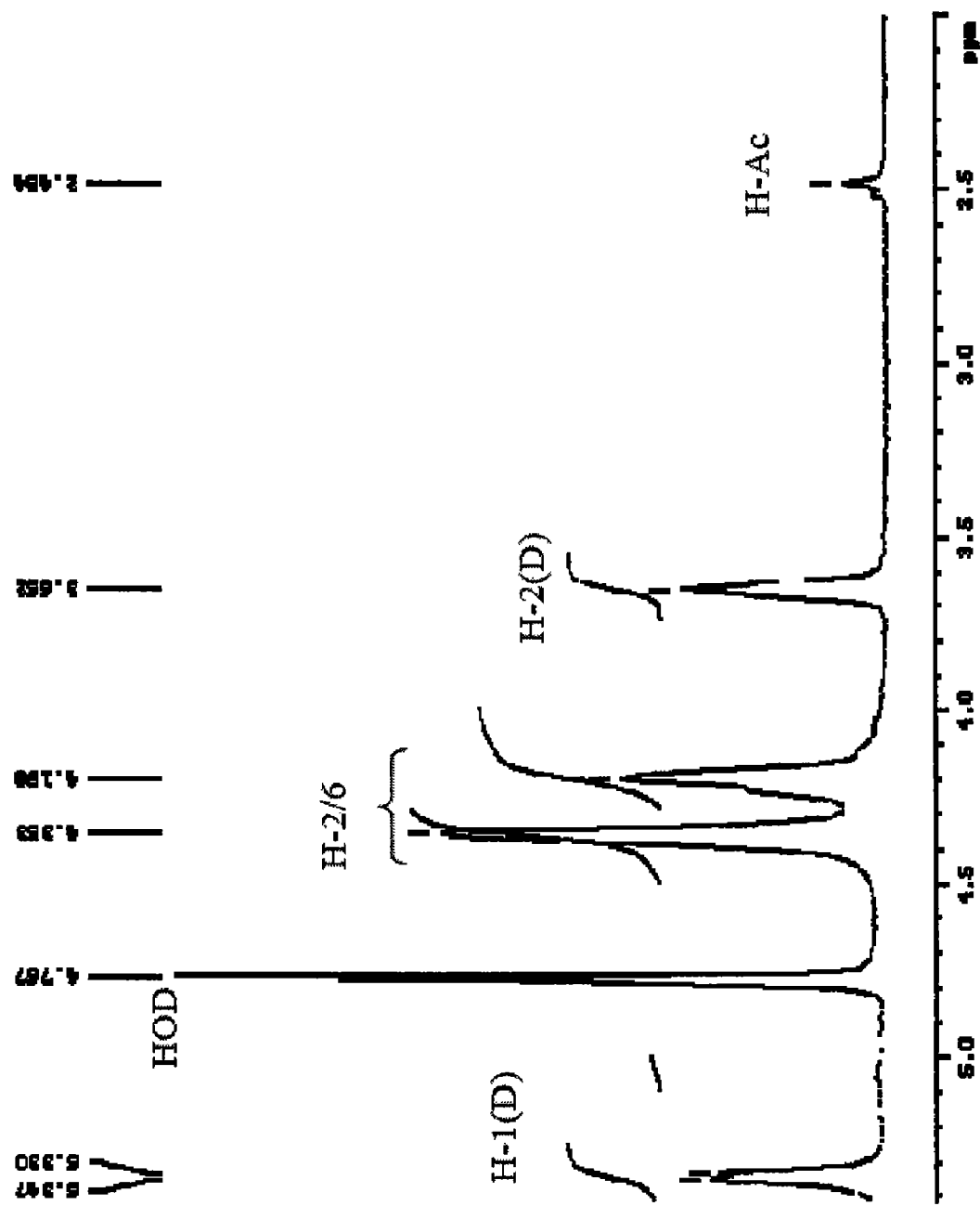
FIG. 5 shows the 400 MHz $^1$H NMR spectra of chitosan with different DDA at 70° C.: (a) alkaline hydrolyzed chitosan (DDA=96.4±0.72%); and (b) commercially available chitosan (DDA=82.5±1.15%).
Figure 5B:
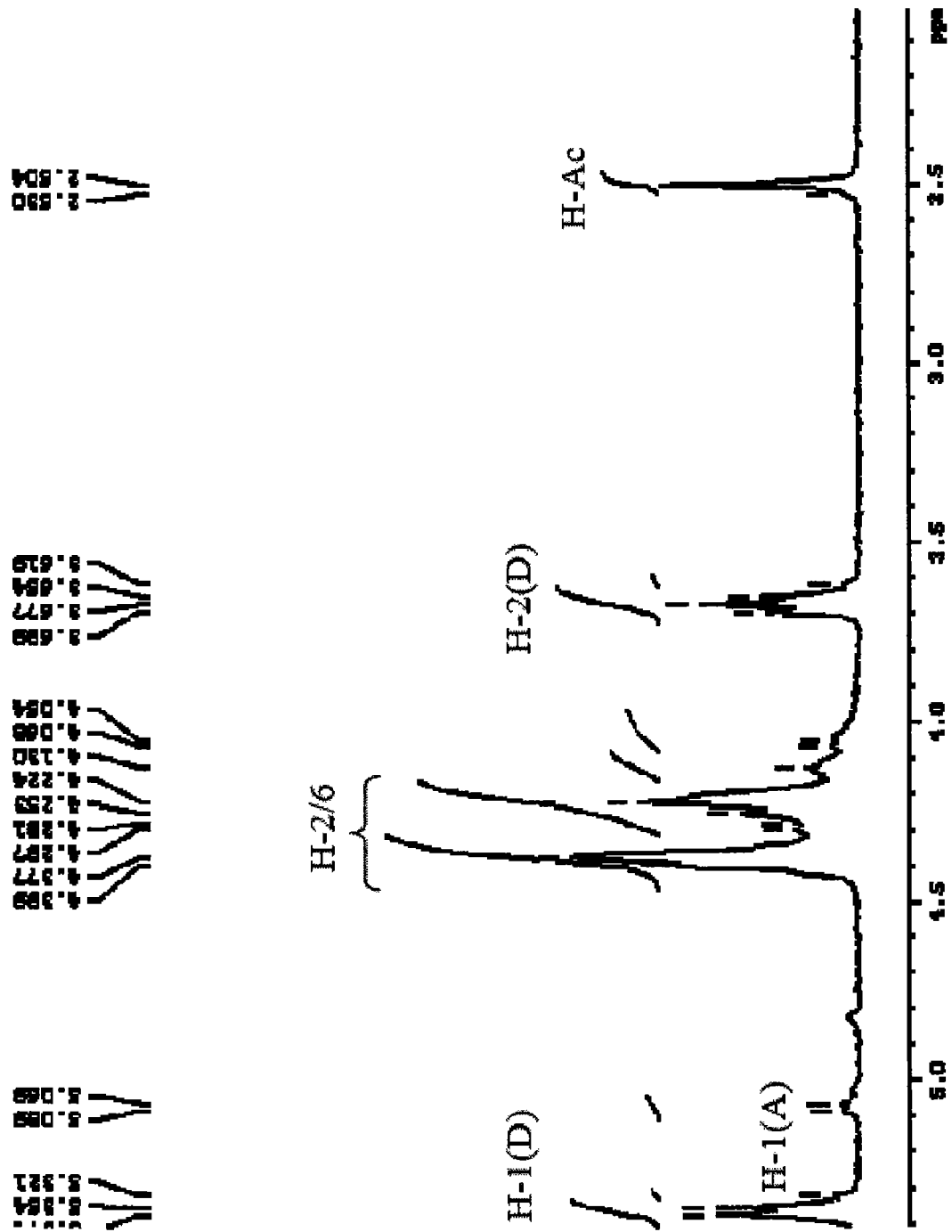

FIG. 5 presents the 400 MHz $^1$H NMR spectra of chitosan with different DDA at 70° C. By alkaline hydrolysis, the DDA of chitosan was successfully adjusted. For repairing longer nerve defects, the rate of resorption of the scaffold is also very critical. Controlling the degree of deacetylation of chitosan can regulate the rate of resorption and mechanical strength. Freier T. et al. showed that chitosan with higher deacetylation had lower degradation rate, higher mechanical strength and cell viability (Freier T. et al., *Biomaterials* 26: 4624-4632 (2005); and Freier T. et al., *Biomaterials* 26: 5872-5878 (2006)).

2.3 Preparation and Characterization of Laminin-Modified Nerve Conduit

Nerve conduits were fabricated by a lyophilizing and wire-heating process (Y. C. Huang et al., 2005, supra). Briefly, Ni—Cr wires (570 um) were used as the mandrel material. The chitosan/acetic acid solution (2% w/v) was injected into the mandrel-filled mold. The mold with wire framework was then put into a liquid nitrogen trap. Once frozen, the Ni—Cr wires were heated by increasing the voltage of the power supplier (Tai Yee Shing, Taiwan). When the power was switched on, the wires were pulled out from the frozen scaffold as soon as possible, usually less than one minute. The wires will be easily removed individually by pulling straight out with pliers. Then, the acetic acid was sublimated using a temperature-controlled lyophilizer (VirTis, NY, USA). After lyopholization, the nerve conduits were first washed by 1:1 0.1 M NaOH-MeOH and 1:1 MeOH-water in order to neutralize the acid, and then dried again by lyophilizers. Finally, the nerve conduits were stored in a dry environment until use. A sharp scalpel blade was used to section the conduit to the desired lengths.

To make the nerve conduits hydrophilic and chemically active, they were first treated with oxygen plasma. The plasma treatment was performed between two parallel plate electrodes in a glow discharge quartz reactor (Model SP100 Plasma System) manufactured by Anatech Co. Ltd of USA. The plasma power supplier was set at 50 W at a frequency of 13.56 MHz. The substrates were placed on the ground electrode facing upward and exposed to the glow discharge at an oxygen pressure of 36 mTorr for 5 and 10 mins for the subsequent laminin (L-2020; Sigma, St. Louis, Mo.) coupling reaction. Then, 200 μl of laminin solution (100 μg/ml) was added onto the plasma pretreated conduits at 4° C. for 3 hrs. After the coupling reaction, the laminin-modified nerve conduits were washed with PBS buffer several times.

The morphology of the laminin-modified nerve conduits was characterized by a light microscope (Olympus IX70, Japan). We used Hematoxylin/Eosin (H&E) staining method to picture the scaffold more clearly. To visualize the protein distribution in the nerve conduits prepared with the plasma technique, representative samples of the conduits were prepared according to the method as described above, but using Rodamine-BSA (red fluorescence) instead of laminin. After preparation, the channels were rinsed in PBS buffer and visualized using a confocal microscope (TCS SP2, Leica, Major Instruments Co., LTD) in the fluorescence mode (FIG. 6A).

Figure 6A:
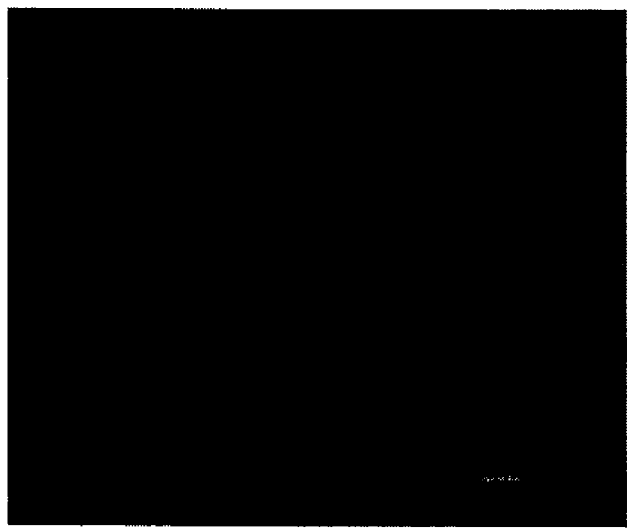
FIG. 6A shows a Rodamine-BSA incorporated nerve conduit detected by fluorescence microscopy (oxygen plasma treatment: 5 mins).

As shown in FIG. 6A, the protein was mainly localized within the nerve conduits. Furthermore, serious pictures also showed the protein appeared to distribute throughout the whole channel wall (data not shown). Localization of laminin in the inner portion of the channel wall should facilitate nerve regeneration, since laminin assists Schwann cells adhesion, and then guides neurite growth. In vivo, this may lead to axon regenerate within the channel and enhanced regenerative capacity.

Figure 6B:
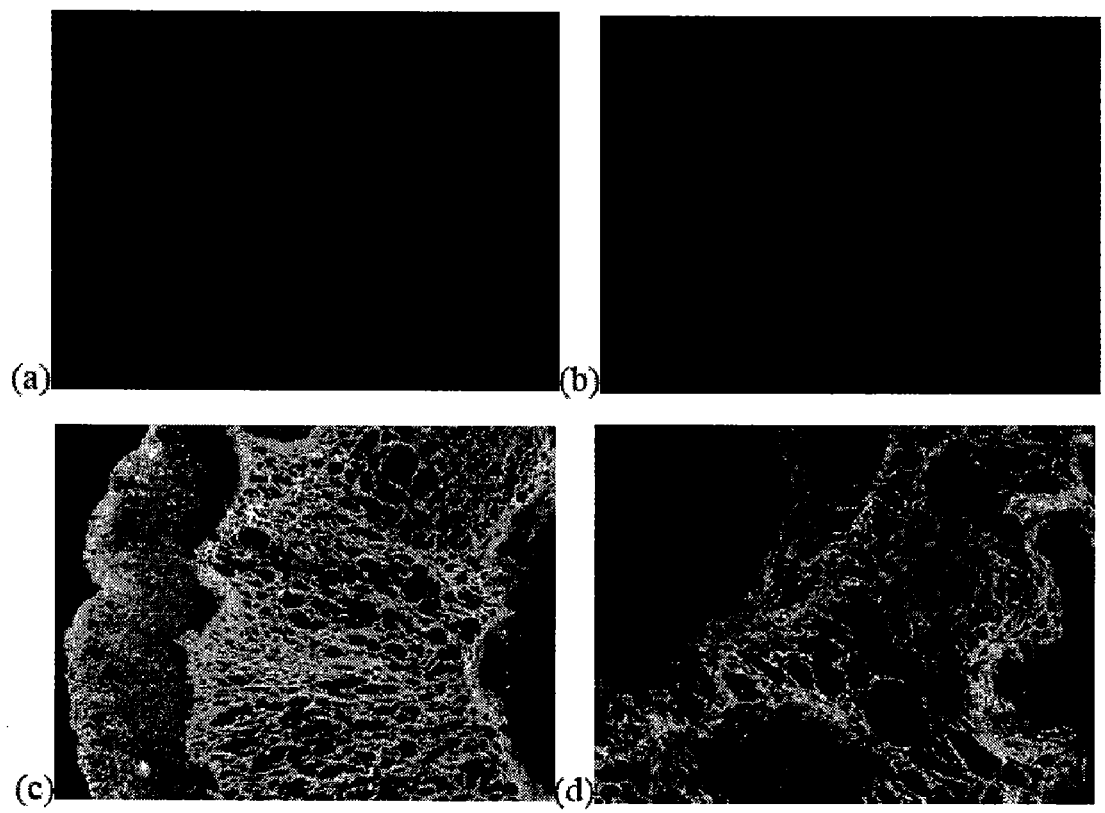
FIG. 6B shows transverse sections of Rodamine incorporated nerve conduits, wherein (a) and (b) are fluorescence images and (c) and (d) are phase contrast images. The conduits were treated by oxygen plasma for either 5 mins (a, c) or 10 mins (b, d).

To observe the changes of the micro-structure of the nerve conduits after oxygen plasma treatment, fluorescence and phase contrast images are shown in FIG. 6B. The more severe the structure destroyed, the longer the plasma treatment time was. Furthermore, the protein penetrated the whole scaffold as 10 minutes plasma treated. The results showed that the unsuitable prolonging of treatment time would result in the loss of micro-architecture of the scaffold. This might guide axon regeneration without orientation.

2.4 Surgical Procedures and Animal Care

Adult 250 g female Sprague-Dawley rats were used in the following studies. All procedures involving animals were approved by the Animals Committee of Taipei Veterans General Hospital. The spinal cords of rats were completely transected at T8 and a 5 mm spinal cord tissue was removed. The 5 mm gap in severed spinal cord was implanted by chitosan conduit. At the specified post-injury times, 1 or 2 months, rats received an overdose of anesthetic sodium pentobarbital. For tissue section staining, the samples in 1-cm long spinal cord segment rostral to the injury site were collected. Rats were perfused with saline followed by 4% buffered paraformaldehyde, and the spinal cords post-fixed (1 h in PFA) and carried through sucrose gradients. Spinal cords were embedded in OCT Tissue Tek mounting media and cut in a cryostat. Serial coronal 10 mm cryo-sections were made and stored at −20° C.

2.5 Behavior Analyses

To ensure that all experimental animals received similar degrees of injury and to monitor the rate of recovery, rats were tested for functional deficits according to the Basso, Beattie and Bresnehan locomotion test (BBB) and the Combined Behavior Score (CBS) after injury (D. M. Basso et al., *J. Neurotrauma* 12: 1-21 (1995)). The BBB tests posture, weight support, and coordination during open field locomotion. The CBS is comprised of a battery of reflex tests that include toe-spread, placing, withdrawal in response to extension, pressure and pain, righting, swimming, and the reflex to lick their paws when placed on a hot surface, and it coordinated motor function including open field mobility, swimming, and ability to maintain position on an inclined plane.

Figure 7A:
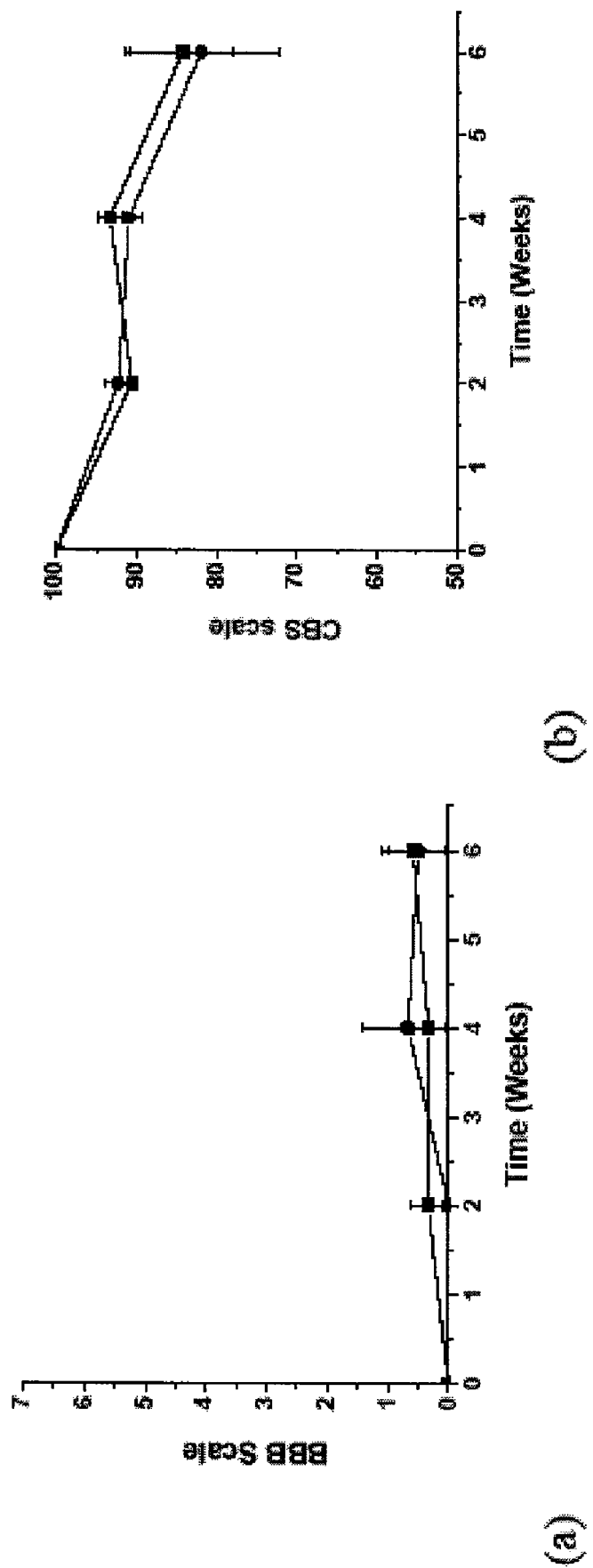
FIG. 7A shows the (a) BBB and (b) CBS scores of the two experimental groups, wherein the red lines represent the group using laminin-modified nerve conduits, while the blue lines represent the group using non-modified nerve conduits (data shown as means±standard deviations, n=3).

FIG. 7A shows the mean BBB and CBS open-field walking scores for the two experimental groups. According to the movies recording the open-field locomotion of representative animals, the injured hind limbs have potential for recovery by the intervention of both laminin-modified nerve conduits and non-modified nerve conduits. The BBB scores of both groups didn't show significant functional recovery, but the CBS scores achieved a stabilized mean of approximately 80, which indicates the onset of behavior improvement. Compared with the group using non-modified nerve conduits, the experimental group using laminin-modified nerve conduits got better results.

The functional recovery of rats was further tested by the treadmill analysis. A robotic rat stepper commercialized by Robomedica, Inc. (Rodent Robot) was used in this study. The robots sampled the body weight support (BWS) level and the positions of the rats' lower shanks and stored these measurements in digital form at 100 Hz on the robot control computer's storage drive. The positions of the rat's lower shanks were calculated from measurements of the robot joint angles made with high precision, rotary, optical encoders, and were accurate to less than 1.0 mm. Detailed evaluations of the rats stepping ability were conducted 14, 28, 35, and 70 days after conduit-transplantation in SCI rats. At the recording, the rats were allowed to step on the treadmill for 30 s, at 75% BWS, without the robots attached. The rats then stepped for 30 s with the robots attached to their hindlimbs at four fixed levels of BWS (75, 50, 25, and 0%). During all training and testing sessions, video recordings of the hindlimb movements were taken in the sagittal-plane. Two types of outcome measures were used to evaluate the stepping ability of the rats on the test days. First, a step detection algorithm was used to count the number of steps performed by each rat at each BWS level. The algorithm identified changes in the direction of the horizontal velocity to indicate toe-off and toe-down events. Limits for the minimum and maximum step length, step duration, velocity were set. Steps that contained at least one parameter outside of these limits were assumed to represent short flexion or large withdrawal movements that were not steps and thus were eliminated from the analyses. The second type of measure used to evaluate stepping ability was qualitative assessment of stepping from video data collected during the test sessions. For each analysis, SCI rats were evaluated on paw placement, weight bearing, and movement ability. The evaluator was blinded to the training group of the rat (i.e., fixed-BWS, ramped-BWS, or untrained). In addition to evaluating stepping ability, the responses of spatial and temporal step characteristics to decreasing BWS were examined. Robot trajectories were segmented into individual steps by the step detection algorithm and then analyzed to determine step length, step height, and toe-off position as well as step cycle, swing, and stance durations as a function of BWS (J. A. Nessler et al., *IEEE Trans Neural Syst Rehabil Eng* 13(4): 497-506 (2005)).

Figure 7B:
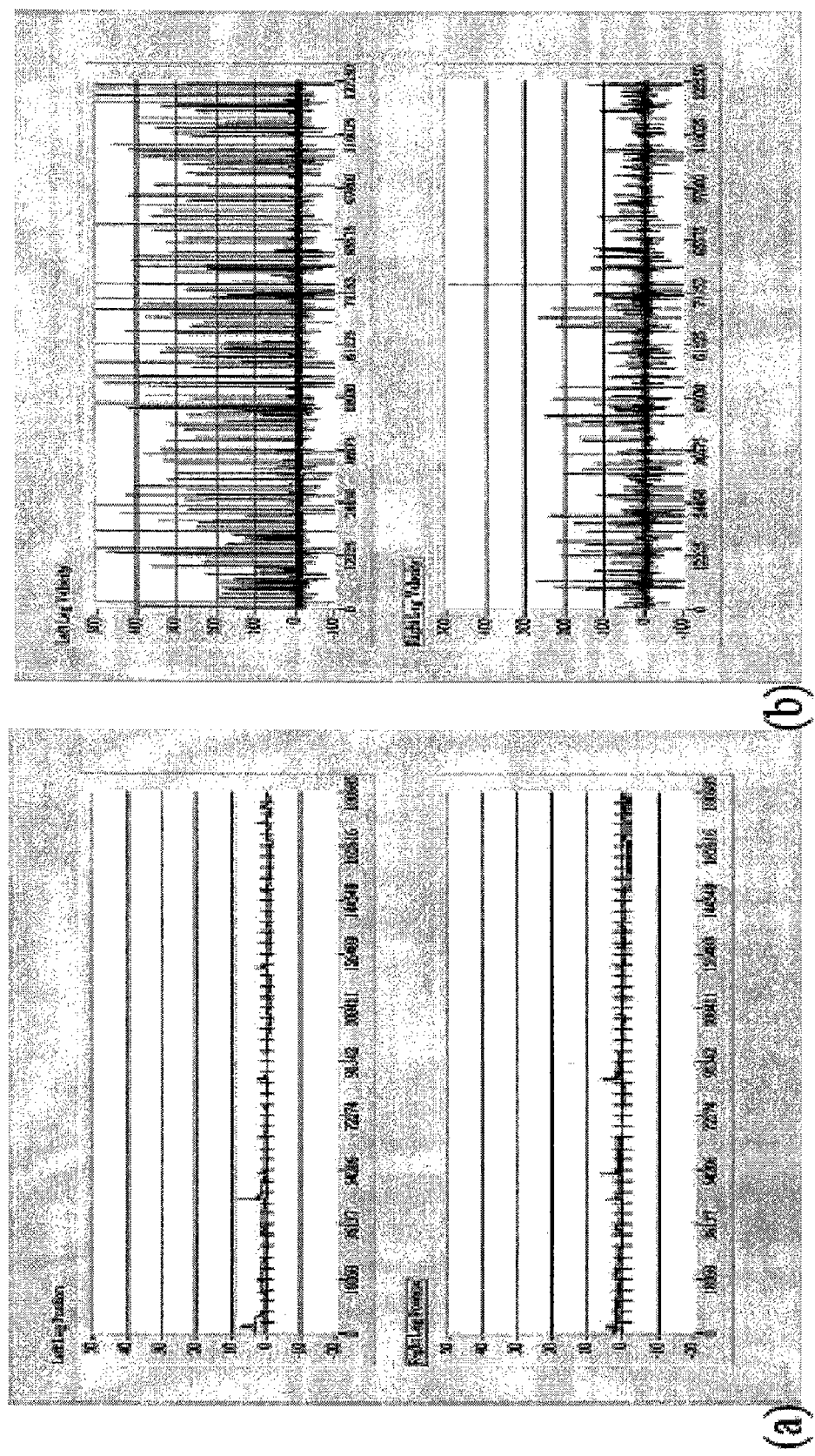
FIG. 7B shows the results of the treadmill analysis of the animals receiving non-modified nerve conduits when (a) spinal cord injury (SCI) just happened and (b) two months post-injury.

As shown in FIG. 7B, the treadmill analysis at two months post-injury could be indicative of plantar-stepping improvement. Therefore, we speculated that the animal functions recovered by both conduits. However, the stepping improvement proved by treadmill analysis might be due to muscular or neural function, which is difficult to differentiate. Therefore, the results gotten from BBB, CBS and treadmill analysis can implicate the tendency of behavior improvement. That is why the immunohistochemistry and histological analysis should be preceded in the following experiments.

2.6 Immunohistochemistry

Histology and immunocytochemistry were performed on all cords to help elucidate functional recovery. The animals were perfused by 4% paraformaldehyde in phosphate buffer. The spinal cords were collected, immersed in 4% paraformaldehyde in phosphate buffer overnight and then transferred to a 30% sucrose solution. Horizontal or transverse cryosection (20 μm thickness) of spinal cords were placed on poly-L-lysine-coated slide for immunostaining. The sections were incubated with the antibodies of interest, washed in PBS, and then incubated in secondary antibodies conjugated with fluorephore, or secondary antibodies coupled with biotin then streptavidin conjugated fluorephore to increase sensitivity. Alternatively, after the primary antibody incubation, the sections can be incubated in ABC mixture (Vector lab) and subsequently develop the peroxidase by incubation in DAB solution to visualize the peroxidase label, or kit from vector lab for chromogen development of desire.

Figure 8A:
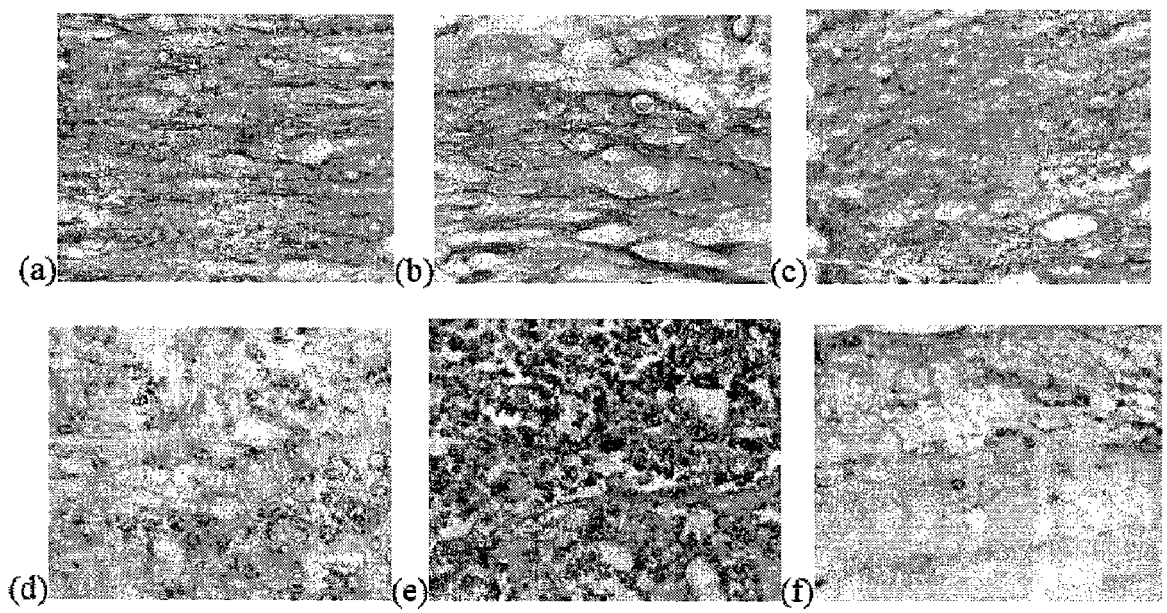
FIG. 8A shows the laminin-modified nerve conduit sections at the injury epicenter, immunostained for (a-c) tubulin beta III, a cytoskeleton marker and (d-f) ED-1, a macrophage marker, wherein the sections of (a) and (d) are at T5 and T6, (b) and (e) are at the lesion area, and (c) and (f) are at T10.

The images of the spinal cord from T5 to T10 presented in FIG. 8A are representative of the laminin-modified group at 30 days post-injury, and were obtained from animals whose CBS scores placed them near the mean of their respective groups. The large number of tubulin beta III-positive cells in the lesion area indicated that lots of cells were found. Furthermore, the ED-1 positive stain showed that macrophage infiltrated the side of injury and remove inhibitory debris.

Macrophage can also produce cytokines to enhance axon re-grow. In order to get the proof directly for axon regeneration, GAP-43, a protein up-regulated in the growth cones of regenerating axons was used. The presence of GAP-43 was confirmed by the use of anti-GAP-43 as primary antibody, and than analyzed by Western blot. For the Western blot analysis, ten sections were removed from one rat's spinal cord. The sections are incubated with 1 mL of 50 mM NH4Cl at room temperature for 10 minutes, and then wash with 1×PBS, and incubated with 1 mL of 50 mM Tris-HCl, pH 7.4 at room temperature (RT) for 10 minutes, and then washed with 1×PBS. Protein samples were extracted from the spinal cord sections in 1% NP-40 lysis buffer and detected using the Bradford protein assay. Equal amounts of protein were loaded on a 3.5-12.5% gradient SDS-PAGE gel. Electrophoresis was performed according to standard procedures and the proteins were transferred to a PVDF membrane which was incubated with anti-GAP-43 as primary-antibody. The membrane was then incubated with HRP-conjugated secondary antibody, and reacted with SuperSignal Chemiluminescent Substrate (Pierce, Rockford, Ill.), and finally the signal was capture by film. The related optic densities of GAP-43 positive bands are quantified by using imageJ (NIH).

Figure 8B:
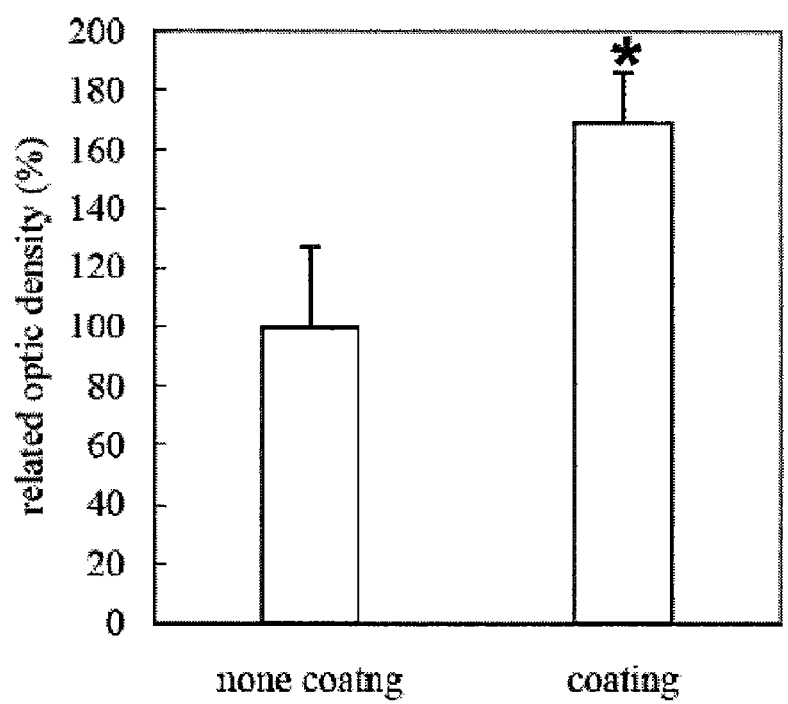
FIG. 8B shows the western blot antibody reactivity of GAP-43, wherein the related optic density was significantly higher in the laminin-modified group marked by the asterisk (student's t test).

The related optic densities of GAP-43 positive bands showed in FIG. 8B suggested that there may be a component of regeneration occurring profile. Compared with the non-modified group, the laminin-modified group had a larger amount of GAP-43 detected. This means the laminin-modified nerve conduit has better efficiency for nerve regeneration.

Figure 8C:
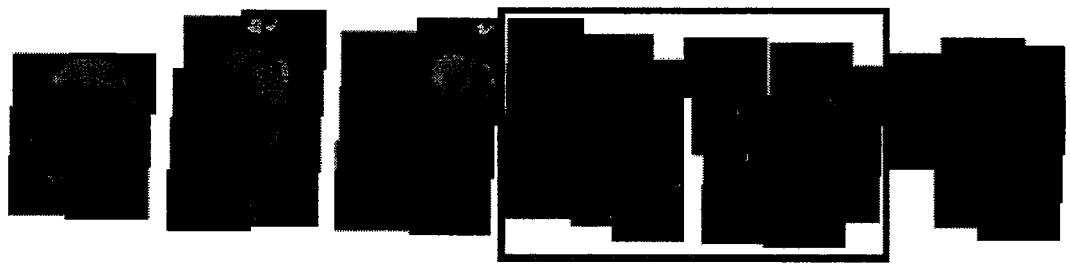
FIG. 8C shows the tubulin staining of the non-modified group at 60 days post-injury, wherein (a) are the transverse sections and (b) are the longitudinal section.
Figure 8C:
Figure 8D:
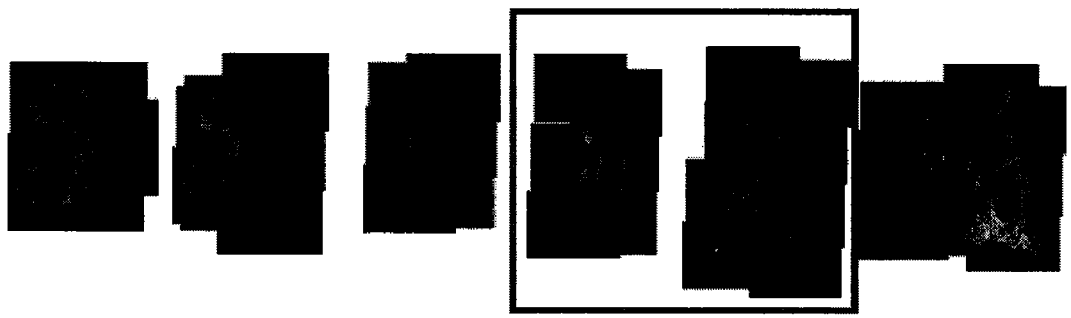
FIG. 8D shows the GAP-43 staining of the non-modified group at 60 days post-injury, wherein (a) are the transverse sections and (b) are the longitudinal section.
Figure 8D:
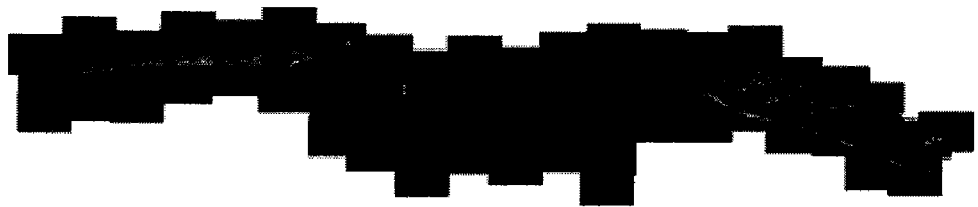

Although nerve regenerated following traumatic SCI as mediated by the nerve conduit, it may be augmented by possible regenerative routes. Transverse sections were obtained from T5 to T10, and the longitudinal sections were cut along the midline of the cord through the injury epicenter (FIG. 8C). The two images in FIG. 8C(a) in the red frame are at the lesion area. A large number of tubulin-positive elements throughout the channel and scaffold further suggested a possible mechanism for cellular growth. In addition to the channel of the conduit, the porous chitosan scaffold also has good affinity for cell attachment. The images immunostained with GAP-43 in FIG. 8D were taken from the same spinal cord area as FIG. 8C. The positive GAP-43 results showed that most GAP-43 distributed around the channel at 60 days post-injury. We propose that the inner surface of nerve conduit may be the best region for axon regeneration.

Figure 8E:
FIG. 8E shows the immunostaining for two other markers of the non-modified group at 60 days post-injury, wherein (a) are longitudinal sections stained for COX-2, and (b) are transverse sections stained for caspase-3.
Figure 8E:

The non-modified nerve conduit exhibited immuno-negative staining for antibodies against either COX-2 or caspase-3 (FIGS. 8E(a) and (b), respectively). In FIG. 8E, the region of immuno-negative staining is within the space of the primary injury, suggesting that the newly formed tissue did not develop inflammatory reaction. The transverse sections in FIG. 8E(b) were cut from T5 to T10 of the spinal cord, and the nerve conduit was at T8. The immunohistology employed a caspase-3 antibody to identify apoptosis. Encouragingly, the negative results showed no apoptosis happened during nerve regeneration.

2.7 Conclusions

Using oxygen plasma, we have successfully incorporated laminin on the inner surface of nerve conduit. Unsuitably prolonged plasma treatment time will destroy the microstructure of the porous chitosan scaffold. For animal modes experiments, the results gotten from BBB, CBS and treadmill analysis after receiving nerve conduits transplantation implicated the tendency of behavior improvement. The immuno-positive stain of ED-1, Tubulin beta III and GAP-43 indicated that the nerve conduit could lead the damaged axons extending through the injured area. The immuno-negative stain of COX-2 and Caspase-3 indicated that the nerve conduits may not trigger unnecessary inflammation and apoptosis post-surgery. By western blot analysis, the optic density of GAP-43 of laminin-modified groups compared better with non-modified ones. Laminin has indeed increased the efficiency of axon growth.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I/we claim:

1. A method for promoting in vivo regeneration of a severed mammalian nerve so as to bridge a gap between severed ends of the nerve, the method comprising bringing the severed ends of the nerve into contact with respective ends of a hollow conduit, the conduit comprising a wall composed of a biodegradable polymeric material, a lumen defined by a lumenal surface of the wall, and laminin covalently bound to functional groups in the lumenal surface of the wall, wherein the functional groups are derived from the biodegradable polymeric material with a gas plasma treatment.

2. The method according to claim 1, wherein:
   (a) the gas plasma treatment is conducted with gas plasma at a power density and a pressure for a time sufficient to activate the biodegradable polymeric material on the lumenal surface to form the functional groups for covalent bonding with laminin; and
   (b) the lumenal surface is contacted with laminin for a time sufficient to allow covalent bond formation between laminin and the functional groups.

3. The method according to claim 1, wherein the biodegradable polymeric material is selected from the group consisting of collagen, poly(lactic acid), poly(glycolic acid), poly(lactic-co-glycolic acid), polycaprolactone, poly(caprolactone-co-lactic acid), chitosan, alginate, hyaluronic acid, gelatin and fibrin.

4. The method according to claim 3, wherein the biodegradable polymeric material comprises poly(lactic-co-glycolic acid).

5. The method according to claim 3, wherein the biodegradable polymeric material comprises chitosan.

6. The method according to claim 1, wherein the gas plasma treatment comprises $O_2$ or $O_2$-containing gas plasma.

7. The method according to claim 2, wherein the gas plasma comprises $O_2$ or $O_2$-containing gas plasma.

8. The method according to claim 2, wherein the power density operating in (a) is about 2 to about 100 W/cm$^2$.

9. The method according to claim 2, wherein the power density operating in (a) is about 50 W/cm$^2$.

10. The method according to claim 2, wherein the pressure operating in (a) is about 0 to about 80 mTorr.

11. The method according to claim 10, wherein the pressure operating in (a) is about 36 mTorr.

12. The method according to claim 2, wherein the time of treatment in (a) is about 5 to 10 minutes.

13. The method according to claim 12, wherein the time of treating in (a) is about 5 minutes.

14. The method according to claim 2, wherein (b) comprises adding to the conduit a solution containing an appropriate concentration of laminin to provide direct contact between the activated functional groups in the lumenal surface and laminin.

15. The method according to claim 14, wherein the laminin solution has a laminin concentration of about 100 μg/ml.

16. The method according to claim 14, wherein the conduit is incubated in the solution at about 4° C. for about 3 hours.

* * * * *